(12) United States Patent
Watanabe et al.

(10) Patent No.: US 6,177,220 B1
(45) Date of Patent: Jan. 23, 2001

(54) STILBENE DERIVATIVE AND METHOD OF PRODUCING THE SAME, AND ELECTROPHOTOSENSITIVE MATERIAL

(75) Inventors: Yukimasa Watanabe; Hirofumi Kawaguchi, both of Osaka (JP)

(73) Assignee: Kyocera Mita Corporation, Osaka (JP)

( * ) Notice: Under 35 U.S.C. 154(b), the term of this patent shall be extended for 0 days.

(21) Appl. No.: 09/422,099

(22) Filed: Oct. 20, 1999

(30) Foreign Application Priority Data

Oct. 29, 1998 (JP) .................................................. 10-308878

(51) Int. Cl.$^7$ ............................ C07C 211/00; G03G 5/06
(52) U.S. Cl. ............................................. 430/73; 564/434
(58) Field of Search ..................... 430/72, 73; 564/434

(56) References Cited

U.S. PATENT DOCUMENTS 6,015,646 * 1/2000 Iwasaki et al. ...................... 430/73
6,022,998 * 2/2000 Kawaguchi et al. ................. 564/434

FOREIGN PATENT DOCUMENTS 50-31773   3/1975   (JP) .
7-244389   9/1995   (JP) .

OTHER PUBLICATIONS

CA 113;221304f; JP 02, 109, 056, Suzuki et al., Apr. 1990.

* cited by examiner

*Primary Examiner*—John Goodrow
(74) *Attorney, Agent, or Firm*—Smith Gambrell & Russell, LLP

(57) ABSTRACT

Disclosed are a stilbene derivative having the general formula (1) and a production thereof, and the electrophotosensitive material comprises a conductive substrate and a photosensitive layer provided on the conductive substrate, wherein the photosensitive layer contains a stilbene derivative (1):

wherein $R^1$ and $R^3$ represent an alkyl group which may have a substituent, an alkoxy group which may have a substituent or the like, and $R^2$ and $R^4$ represent a hydrogen atom, an alkyl group which may have a substituent or the like.

13 Claims, 2 Drawing Sheets

STILBENE DERIVATIVE AND METHOD OF PRODUCING THE SAME, AND ELECTROPHOTOSENSITIVE MATERIAL

BACKGROUND OF THE INVENTION

The present invention relates to a stilbene derivative having excellent electric charge transferring capability and a method of producing the same, and an electrophotosensitive material containing the stilbene derivative, which is used in image forming apparatuses such as electrostatic copying machine, facsimile, laser beam printer and the like.

In the image forming apparatuses, various organic photoconductors having a sensitivity within a wavelength range of a light source used in said apparatuses have been used. These organic photoconductors have widely been used because of easier production than that in the case of a conventional inorganic photoconductor, various selective photosensitive materials (e.g. electric charge transferring material, electric charge generating material, binding resin, etc.) and high design freedom.

Examples of the organic photoconductor include a single-layer type photoconductor wherein an electric charge transferring material and an electric charge generating material are dispersed in the same photosensitive layer, and a multi-layer photoconductor comprising an electric charge generating layer containing an electric charge generating material and an electron transferring layer containing an electron transferring material, which are mutually laminated.

As the electric charge transferring material used in the above organic photoconductor, a stilbene derivative is disclosed in Japanese Patent Kokai Publication Nos. 31773/1975 and 244389/1996.

However, since the stilbene derivative disclosed in the above publications is usually inferior in compatibility with a binding resin and is not uniformly dispersed in the photosensitive layer, electric charges hardly move. Therefore, although the above stilbene derivative itself has high electric charge mobility, when using this stilbene derivative as the electric charge transferring material in the photoconductor, its characteristics can not be sufficiently exhibited. Accordingly, the residual potential of the photoconductor becomes higher and the photosensitivity becomes insufficient.

SUMMARY OF THE INVENTION

Thus, an object of the present invention is to solve the above technical problems and to provide a novel stilbene derivative suited for use an electric charge transferring material of the electrophotosensitive material, and a method of producing the same.

Another object of the present invention is to provide an electrophotosensitive material whose sensitivity is improved compared with the prior art.

The present inventors have intensively studied to attain the above objects and found a new fact that a compound, wherein diphenylamino groups at a molecular end are not symmetric and one phenyl group of the diphenylamino group has no substituent while at least the other phenyl group has a substituent at the 2 (ortho, o-) position, has better compatibility with a binder resin than that of a conventional stilbene derivative and large electric charge mobility, thus completing the present invention.

That is, the stilbene derivative of the present invention is characterized in that it is represented by the general formula (1):

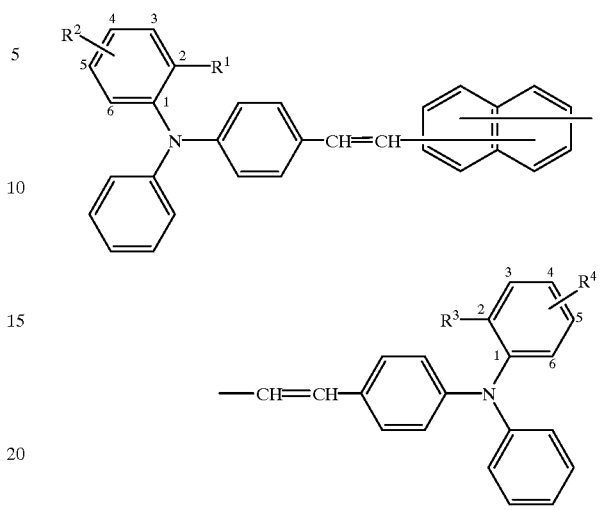

(1)

wherein $R^1$ and $R^3$ are the same or different and represent an alkyl group which may have a substituent, an aryl group which may have a substituent, an aralkyl group which may have a substituent, or an alkoxy group which may have a substituent, and $R^2$ and $R^4$ are the same or different and represent a hydrogen atom, an alkyl group which may have a substituent, or an alkoxy group which may have a substituent.

The stilbene derivative represented by the general formula (1) according to the present invention is a compound wherein one phenyl ring of the diphenylamino group is substituted at the 2 (ortho, o-) position, which is not specifically disclosed in Japanese Patent Kokai Publication Nos. 7-244389 and 50-31773, and has high compatibility with a binding resin and high electric charge mobility in comparison with the compounds disclosed in the above publications.

Accordingly, a high-sensitivity electrophotosensitive material can be obtained by using such a stilbene derivative (1) as an electric charge (hole) transferring material in the electrophotosensitive material.

Furthermore, in order to obtain an electrophotosensitive material having higher sensitivity, it is preferred to use a stilbene derivative, wherein one phenyl group of the diphenylamino group at the molecular end has no substituent while the other phenyl group has a substituent at the 2-/3-positions, 2-/5-positions or 2-/6-positions or has a substituent only at the 2-position (i.e. stilbene derivative wherein the 4 (para, para-) position is a hydrogen atom) among the above stilbene derivative (1).

The present inventors have studied about a method of efficiently producing a formyl compound (2) of triphenylamine described below, as a starting material, in the method of producing the above stilbene derivative (1). As a result, they have found a new fact that, when a triphenylamine derivative (5) having a substituent at the 2-position of the phenyl group is formylated by the Vilsmeier method, the above compound (2), wherein the phenyl group having a substituent among three phenyl groups of the compound (5) is not formylated and only non-substituted phenyl group is formylated, can be efficiently produced, resulting in improvement of the productivity of the stilbene derivative (1). Thus, the present invention has been accomplished.

That is, the method of producing the stilbene derivative (1) of the present invention is characterized by reacting a formylated triphenylamine derivative represented by the general formula (2):

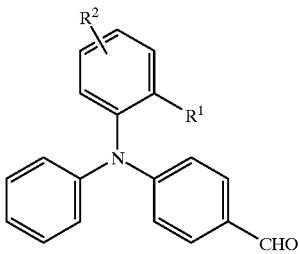

(2)

wherein R¹ represent an alkyl group which may have a substituent, an aryl group which may have a substituent, an aralkyl group which may have a substituent, or an alkoxy group which may have a substituent, and R² represents a hydrogen atom, an alkyl group which may have a substituent, or an alkoxy group which may have a substituent, with a bisphosphate derivative represented by the general formula (3):

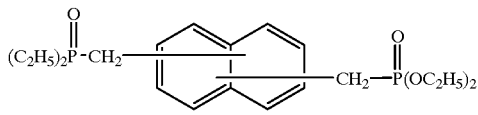

(3)

The above formylated triphenylamine derivative (2) used in the production method of the present invention is a compound obtained by reacting an aniline derivative represented by the general formula (4):

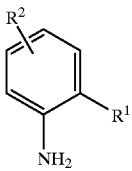

(4)

wherein R¹ represent an alkyl group which may have a substituent, an aryl group which may have a substituent, an aralkyl group which may have a substituent, or an alkoxy group which may have a substituent, and R² represents a hydrogen atom, an alkyl group which may have a substituent, or an alkoxy group which may have a substituent, with iodobenzene to obtain a triphenylamine derivative represented by the general formula (5):

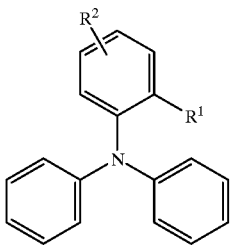

(5)

wherein R¹ represent an alkyl group which may have a substituent, an aryl group which may have a substituent, an aralkyl group which may have a substituent, or an alkoxy group which may have a substituent, and R² represents a hydrogen atom, an alkyl group which may have a substituent, or an alkoxy group which may have a substituent, and formylating this compound (5) by using the Vilsmeier method.

The reason why only the formyl compound (2) of triphenylamine as the raw material of the stilbene derivative (1) is produced in high yield when the above triphenylamine derivative (5) is formylated by the Vilsmeier method is not apparent. However, regarding the phenyl group having a substituent R¹ at the ortho-position among three phenol groups of the compound (5), an axis of bonding between the nitrogen atom and phenyl group in the compound (5) is distorted by an influence of the substituent R¹ and giving and receiving of electrons from the nitrogen atom become poor and, therefore, nucleophilicity of the phenyl group is lowered in comparison with the other phenyl. As a result, the phenyl group is not formylated at the para-position and the other phenyl group is formylated only at the para-position.

The electrophotosensitive material of the present invention is an electrophotosensitive material comprising a conductive substrate and a photosensitive layer provided on the conductive substrate, characterized in that the photosensitive layer contains a stilbene derivative represented by the above general formula (1).

Since the electrophotosensitive material of the present invention contains the stilbene derivative represented by the above general formula (1) in the photosensitive layer, the rate of transferring electric charges (holes) generated in the electric charge generating material is fast, that is, the electric charge mobility is large and the photosensitivity at the time of charging and exposure is excellent. As a result, according to the electrophotosensitive material of the present invention, high sensitivity can be obtained in comparison with the case where a conventional stilbene derivative is used as the hole transferring material.

The photosensitive layer is preferably a single-layer type photosensitive layer containing an electric charge generating material and electron transferring material, together with the stilbene derivative represented by the above general formula (1).

The stilbene derivative (1) of the present invention has high compatibility with the binder resin and has high electric charge transferring capability (hole transferring capability).

The electrophotosensitive material of the present invention has high sensitivity because the stilbene derivative (1) is used as the hole transferring material. Accordingly, the electrophotosensitive material of the present invention has such peculiar operation/working-effect that it contributes to realization of high speed and high performance of various image forming apparatuses such as antistatic copying machine, facsimile, laser beam printer and the like.

DETAILED EXPLANATION OF THE INVENTION

Figure 1:
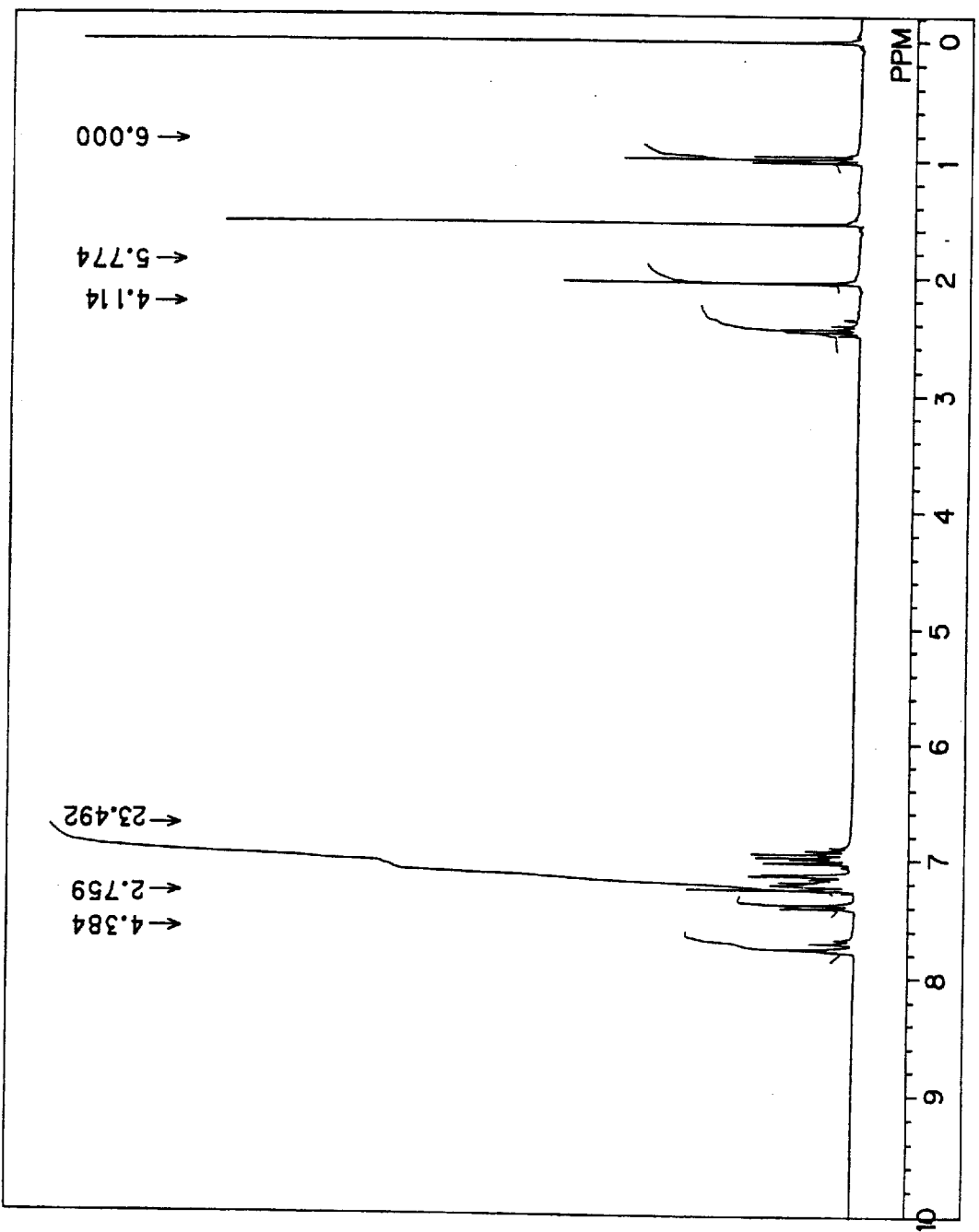
FIG. 1 is a graph showing a ¹H-NMR spectrum of the stilbene derivative (11-6).

First, the stilbene derivative (1) of the present invention will be described in detail.

In the general formula (1), examples of the alkyl group corresponding to $R^1$, $R^2$, $R^3$ and $R^4$ include alkyl groups having 1 to 6 carbon atoms, such as methyl, ethyl, n-propyl, isopropyl, n-butyl, isobutyl, s-butyl, t-butyl, pentyl, isopentyl, neopentyl, hexyl and the like. Among them, alkyl groups having 1 to 4 carbon atoms, such as methyl, ethyl, n-propyl, isopropyl, n-butyl, isobutyl, s-butyl, t-butyl and are preferred.

Alkyl groups corresponding to $R^1$, $R^2$, $R^3$ and $R^4$ may have a substituent, and specific examples thereof include hydroxyalkyl group, alkoxyalkyl group, monoalkylaminoalkyl group, dialkylaminoalkyl group, halogen-substituted alkyl group, alkoxycarbonylalkyl group, carboxyalkyl group, alkanoyloxyalkyl group, amionoalkyl group and the like.

In the stilbene derivative of the present invention, the substituent is preferably an alkyl group having an electron donative group, such as alkoxy group, monoalkylamino group, amino group, dialkylamino group or the like in view of enhancement in electric charge mobility.

Examples of the above hydroxyalkyl group include hydroxyalkyl groups whose alkyl portion has 1 to 6 carbon atoms, such as hydroxymethyl, 2-hydroxyethyl, 1,1-dimethyl-2-hydroxyethyl, 3-hydroxypropyl, 4-hydroxybutyl, 2-hydroxybutyl, 1-hydroxypentyl, 6-hydroxyhexyl and the like.

Examples of the above alkoxyalkyl group include alkoxyalkyl groups whose alkyl portion and alkoxy portion have 1 to 6 carbon atoms, such as methoxymethyl, methoxyethyl, methoxybutyl, ethoxyhexyl, ethoxymethyl, butoxyethyl, t-butoxyhexyl, hexyloxymethyl and the like.

Examples of the above monoalkylaminoalkyl group include alkylaminoalkyl groups whose alkyl portion has 1 to 6 carbon atoms, such as methylaminoethyl, ethylaminoethyl, hexylaminomethyl, ethylaminoethyl, hexylaminoethyl, methylaminopropyl, butylaminopropyl, methylaminobutyl, ethylaminobutyl, hexylaminobutyl, methylaminohexyl, ethylaminohexyl, butylaminohexyl, hexylaminohexyl and the like.

Examples of the above dialkylaminoalkyl include dialkylaminoalkyl groups whose alkyl portion has 1 to 6 carbon atoms, such as dimethylaminoethyl, diethylaminoethyl, dihexylaminomethyl, diethylaminoethyl, dihexylaminoethyl, dimethylaminopropyl, dibutylaminopropyl, dimethylaminobutyl, diethylaminobutyl, dihexylaminobutyl, dimethylaminohexyl, diethylaminohexyl, dibutylaminohexyl, dihexylaminohexyl and the like.

Examples of the above alkoxycarbonylalkyl group include alkoxycarbonylalkyl groups whose alkyl portion and alkoxy portion have 1 to 6 carbon atoms, such as methoxycarbonylmethyl, methoxycarbonylethyl, methoxycarbonylhexyl, ethoxycarbonylmethyl, ethoxycarbonylethyl, propoxycarbonylmethyl, isopropoxycarbonylmethyl, butoxycarbonylmethyl, pentyloxycarbonylmethyl, hexyloxycarbonylmethyl, hexylcarbonylbutyl, hexylcarbonylhexyl and the like.

Examples of the above carboxyalkyl group include carboxyalkyl groups whose alkyl portion has 1 to 6 carbon atoms, such as carboxymethyl, carboxyethyl, carboxybutyl, carboxyhexyl, 1-methyl-2-carboxyethyl and the like.

Examples of the above halogen-substituted alkyl group include alkyl groups having 1 to 6 carbon atoms, which are substituted with 1 to 3 halogen atoms, such as monochloromethyl, monobromomethyl, monoiodomethyl, monofluoromethyl, dichloromethyl, dibromomethyl, diiodomethyl, difluoromethyl, trichloromethyl, tribromomethyl, triiodomethyl, trifluoromethyl, monochloroethyl, monobromoethyl, monoiodoethyl, monofluoroethyl, dibromobutyl, diodobutyl, difluorobutyl, chlorohexyl, bromohexyl, iodohexyl, fluorohexyl and the like.

Examples of the alkanoyloxyalkyl group include alkanoyloxy groups having $C_{2-6}$ alkanoyl portion and $C_{1-6}$ alkyl portion, such as acetoxymethyl, 2-acetoxyethyl, propionyloxymethyl, 1-hexanoyloxy-2-methylpentyl and the like.

Examples of the above aminoalkyl group include aminoalkyl groups whose alkyl portion has 1 to 6 carbon atoms, such as aminomethyl, aminoethyl, aminopropyl, aminobutyl, aminohexyl and the like.

Examples of the alkoxy group corresponding to $R^1$, $R^2$, $R^3$ and $R^4$ include alkoxy groups having 1 to 6 carbon atoms, such as methoxy, ethoxy, isopropoxy, butoxy, t-butoxy, pentyloxy, hexyloxy and the like. The alkoxy group corresponding to $R^1$, $R^2$, $R^3$ and $R^4$ may have a substituent, and examples of the substituent include the same substituents as those described above, such as halogen atom, amino group, hydroxyl group, carboxyl group, alkanoyloxy group and the like.

Examples of the aryl group corresponding to $R^1$ and $R^3$ include phenyl, naphthyl, anthryl, phenanthryl and the like.

Examples of the aralkyl group corresponding to $R^1$ and $R^3$ include aralkyl groups whose alkyl portion has 1 to 6 carbon atoms, such as benzyl, 1-phenylethyl, 3-phenylpropyl, 4-phenylbutyl, 5-phenylpentyl, 6-phenylhexyl and the like.

The above aryl group and aralkyl group may have a substituent, and examples of the substituent include alkyl groups having 1 to 6 carbon atoms which may have a substituent and alkoxy groups having 1 to 6 carbon atoms which may have a substituent, in addition to halogen atom, amino group, hydroxyl group, optionally esterified carboxyl group and cyano group. The substitution position of these substituents is not specifically limited.

The stilbene derivative (1) of the present invention include various stilbene derivatives having different substitution positions of the center naphthalene ring. Among them, stilbene derivatives represented by the following general formulas (11) to (13) are particularly preferred.

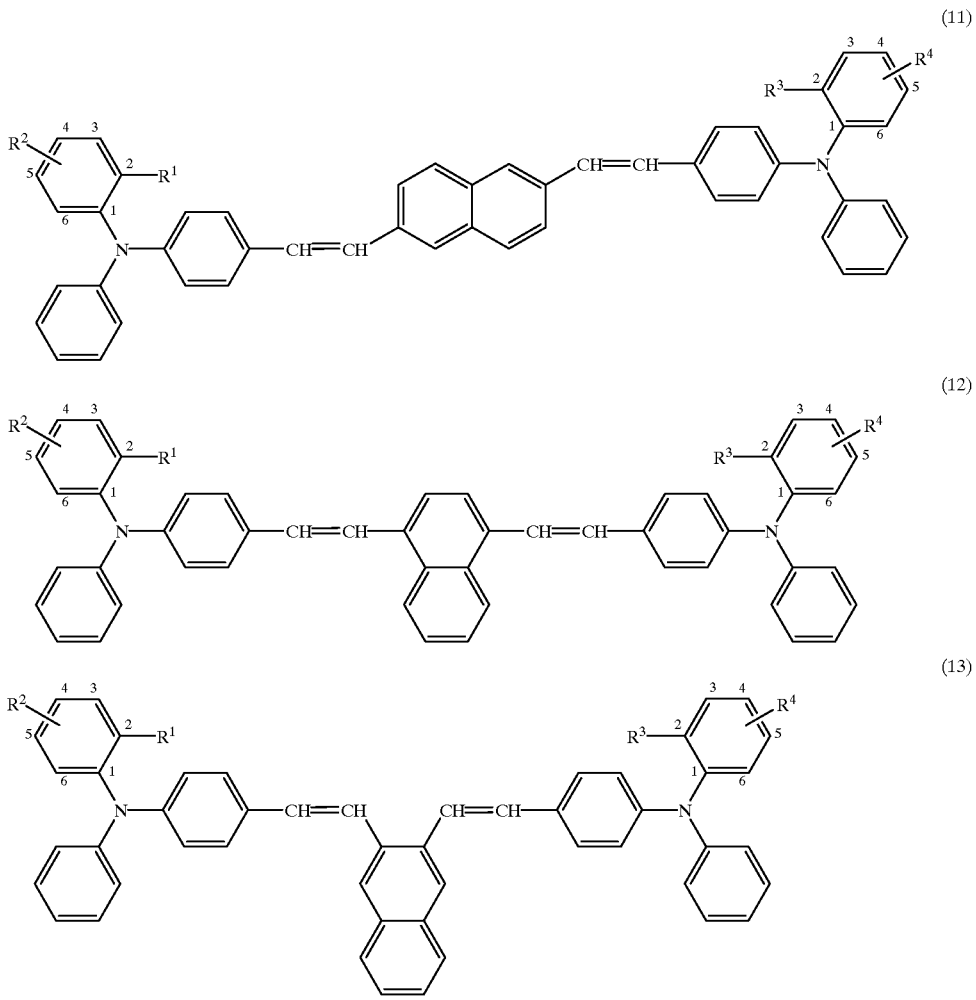

wherein $R^1$ to $R^4$ are as defined above.

As the specific examples of the stilbene derivative represented by the above general formula (1), substituents corresponding to $R^1$ to $R^4$ are shown in the following Tables 1 to 3. In Tables 1 to 3, those represented by a series of the compound numbers (11-1, 11-2, 11-3, . . . ) are stilbene derivatives included in the general formula (11), those represented by a series of the compound numbers (12-1, 12-2, 12-3, . . . ) are stilbene derivatives included in the general formula (12), and those represented by a series of the compound numbers (13-1, 13-2, 13-3, . . . ) are stilbene derivatives included in the general formula (13).

In Tables 3 to 4, H represents a hydrogen atom, Me represents a methyl group, Et represents an ethyl group, i-Pr represents an isopropyl group, t-Bu represents a t-butyl group, MeO represents a methoxy group, EtO represents an ethoxy group, Ph represents a phenyl group, and Bzl represents a benzyl group.

TABLE 1

| Compound number | $R^1$ | $R^2$ | $R^3$ | $R^4$ |
|---|---|---|---|---|
| 11-1 | Me | H | Me | H |
| 11-2 | Me | 6-Me | Me | 6-Me |

TABLE 1-continued

| Compound number | $R^1$ | $R^2$ | $R^3$ | $R^4$ |
|---|---|---|---|---|
| 11-3 | Me | 3-Me | Me | 3-Me |
| 11-4 | Me | 5-Me | Me | 5-Me |
| 11-5 | Et | H | Et | H |
| 11-6 | Et | 6-Me | Et | 6-Me |
| 11-7 | Et | 6-Et | Et | 6-Et |
| 11-8 | i-Pr | H | i-Pr | H |
| 11-9 | i-Pr | 6-Me | i-Pr | 6-Me |
| 11-10 | t-Bu | H | t-Bu | H |
| 11-11 | t-Bu | 5-t-Bu | t-Bu | 5-t-Bu |
| 11-12 | Ph | H | Ph | H |
| 11-13 | Bzl | H | Bzl | H |
| 11-14 | MeO | H | MeO | H |
| 11-15 | EtO | H | EtO | H |
| 11-16 | MeO | 6-Me | MeO | 6-Me |
| 11-17 | MeO | 5-Me | MeO | 5-Me |
| 11-18 | Me | 5-MeO | Me | 5-MeO |

TABLE 2

| Compound number | $R^1$ | $R^2$ | $R^3$ | $R^4$ |
|---|---|---|---|---|
| 12-1 | Me | H | Me | H |
| 12-2 | Me | 6-Me | Me | 6-Me |
| 12-3 | Me | 3-Me | Me | 3-Me |
| 12-4 | Me | 5-Me | Me | 5-Me |
| 12-5 | Et | H | Et | H |
| 12-6 | Et | 6-Me | Et | 6-Me |
| 12-7 | Et | 6-Et | Et | 6-Et |
| 12-8 | i-Pr | H | i-Pr | H |
| 12-9 | i-Pr | 6-Me | i-Pr | 6-Me |
| 12-10 | t-Bu | H | t-Bu | H |
| 12-11 | t-Bu | 5-t-Bu | t-Bu | 5-t-Bu |
| 12-12 | Ph | H | Ph | H |
| 12-13 | Bzl | H | Bzl | H |
| 12-14 | MeO | H | MeO | H |
| 12-15 | EtO | H | EtO | H |
| 12-16 | MeO | 6-Me | MeO | 6-Me |
| 12-17 | MeO | 5-Me | MeO | 5-Me |
| 12-18 | Me | 5-MeO | Me | 5-MeO |

TABLE 3

| Compound number | $R^1$ | $R^2$ | $R^3$ | $R^4$ |
|---|---|---|---|---|
| 13-1 | Me | H | Me | H |
| 13-2 | Me | 6-Me | Me | 6-Me |
| 13-3 | Me | 3-Me | Me | 3-Me |
| 13-4 | Me | 5-Me | Me | 5-Me |
| 13-5 | Et | H | Et | H |
| 13-6 | Et | 6-Me | Et | 6-Me |
| 13-7 | Et | 6-Et | Et | 6-Et |
| 13-8 | i-Pr | H | i-Pr | H |
| 13-9 | i-Pr | 6-Me | i-Pr | 6-Me |
| 13-10 | t-Bu | H | t-Bu | H |
| 13-11 | t-Bu | 5-t-Bu | t-Bu | 5-t-Bu |
| 13-12 | Ph | H | Ph | H |
| 13-13 | Bzl | H | Bzl | H |
| 13-14 | MeO | H | MeO | H |
| 13-15 | EtO | H | EtO | H |
| 13-16 | MeO | 6-Me | MeO | 6-Me |
| 13-17 | MeO | 5-Me | MeO | 5-Me |
| 13-18 | Me | 5-MeO | Me | 5-MeO |

The stilbene derivative (1) of the present invention includes a cis-isomer represented by the following general formula (1-1) and a trans-isomer represented by the following general formula (1-2), each has a different position of a center naphthalene ring and a peripheral substituent: triphenylamine to >C=C<.

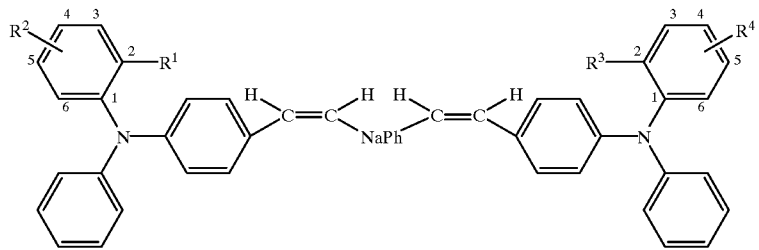

(1-1)

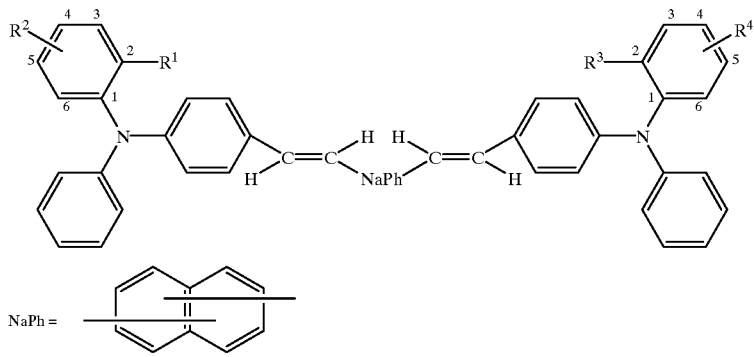

(1-2)

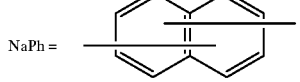

wherein $R^1$ to $R^4$ are as defined above.

It is preferred to use the trans-isomer (1-2) in the electrophotosensitive material of the present invention.

The method of synthesizing the stilbene derivative (1) of the present invention will be described with reference to the case where $R^1$ and $R^3$ are the same groups and $R^2$ and $R^4$ are the same groups as the example.

Reaction scheme (I)

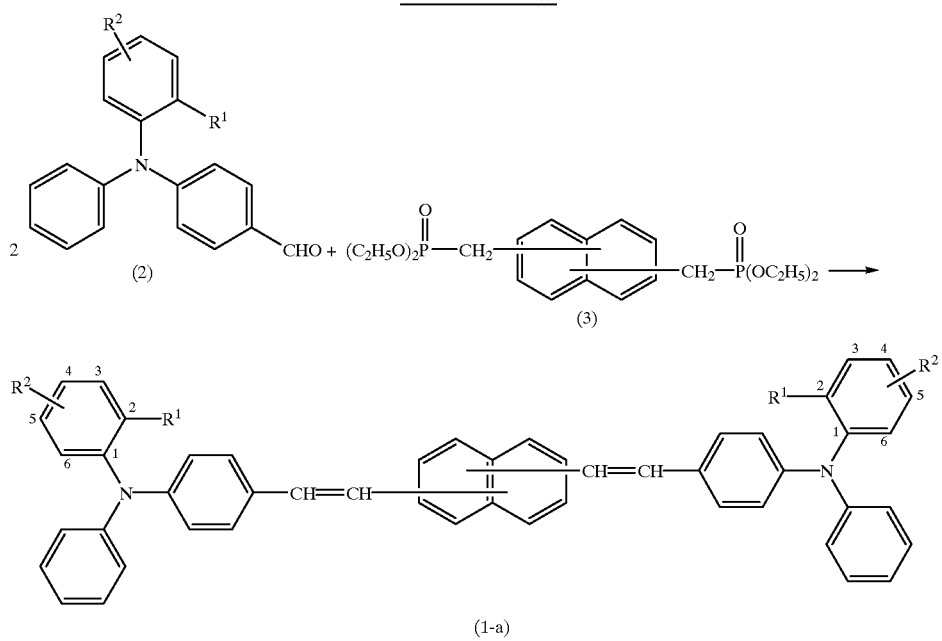

wherein $R^1$ and $R^2$ are as defined above.

According to this reaction, a stilbene derivative of the present invention is obtained by reacting a formyl compound of triphenylamine represented by the general formula (2) with a bisphosphate derivative (3) in a proper anhydrous solvent in the presence of a base.

The solvent used in the above reaction may be any one which does not exert an influence on the reaction, and examples thereof include ethers such as diethyl ether, tetrahydrofuran, dioxane, etc.; halogenated hydrocarbons such as methylene chloride, chloroform, dichloroethane, etc.; and aromatic hydrocarbons such as benzene, toluene, etc.

Examples of the base include sodium alkoxide such as sodium methoxide and metal hydride such as sodium hydride.

The amount of the base is at least 2 to 4 mol, and preferably from 2 to 2.5 mol, per mol of the bisphosphate derivative (3).

The amount of the compound (2) is from 1.8 to 2.5 mol, and preferably from 1.95 to 2.05, per mol of the bisphosphate derivative (3). The reaction is usually conducted at −10 to 25° C., and is complete within the range from about 3 to 12 hours.

Reaction scheme (II)

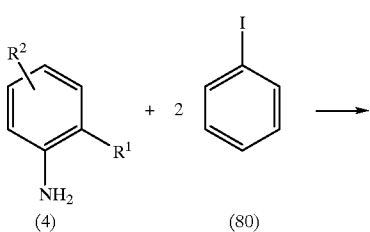

-continued

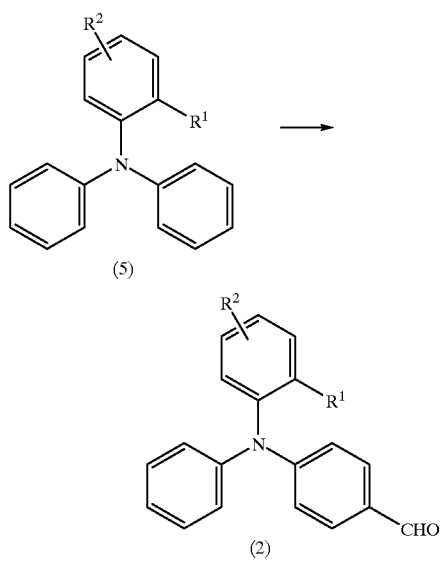

wherein $R^1$ and $R^2$ are as defined above.

According to this reaction, a formyl compound (2) of triphenylamine as a starting material of the above reaction scheme (1-a) is obtained by adding an aniline derivative (4) and iodobenzene (80) in nitrobenzene, reacting them, together with a catalyst such as anhydrous potassium carbonate, copper or the like to obtain a triphenylamine derivative (5) and formylating this triphenylamine derivative (5) by the Vilsmeirer method.

The ratio of the above aniline derivative (4) to iodobenzene (80) to be used is from 1:1.7 to 1:3, and preferably from 1:1.8 to 1:2.2, in a molar ratio. The reaction is usually conducted at 160 to 220° C., and is completed within the range from about 4 to 30 hours.

A reagent (Vilsmeirer reagent used in the above Vilsmeirer method is prepared by a combination of (i) a halogenating agent such as phosphorous oxychloride, phosgene, oxalyl chloride, thionyl chloride, triphenylphosphine-bromine, hexachlorotriphosphazatriene or the like with (ii) N,N-dimethylformamide (DMF), N-methylformanilide (MFA), N-formylmorpholine, N,N-diisopropylformamide or the like. In the present invention, a combination of phosphorous oxychloride with DMF, which can also be used as the solvent, is used, particularly preferably.

In the preparation of the above Vilsmeirer reagent, the ratio of the above (i) to (ii) to be used is usually from 1:1 to 1:2, and preferably from 1:1 to 1:1.2.

The amount of the above Vilsmeirer reagent is from 0.9 to 2 mol, and preferably from 1 to 1.1 mol, per mol of the triphenylamine derivative (5). The formylation of the above compound (5) is usually conducted at 40 to 80° C., and is completed within the range from about 2 to 5 hours.

In the case of synthesizing the stilbene derivative (1) of the present invention wherein $R^1$ and/or $R^2$ are alkyl groups having a substituent, e.g. stilbene derivative (1-x) wherein $R^1$ is a hydroxylalkyl group, (1) the stilbene derivative (1-x) may be synthesized by using an aniline derivative having a hydroxyalkyl group as a starting material, and (2) the stilbene derivative (1-x) may also be synthesized by synthesizing a stilbene derivative (1-xx) wherein $R^1$ is an alkyl group and converting the alkyl group into a hydroxyalkyl group using a conventional method (e.g. oxidation).

Reaction scheme (III)

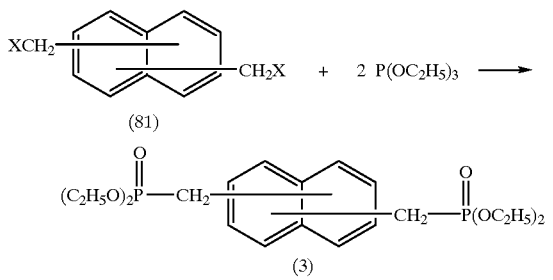

(3)

Wherein X is a halogen atom.

According to this reaction, a bisphosphate derivative (3) as a starting material of the above reaction scheme (1) is obtained by reacting bishalogenomethylnaphtalene (81) with a phosphorous acid triester with or without using a proper solvent. In that case, when tertiary amine is added, a halogenated alkyl is removed from the reaction system and the reaction is promoted.

The solvent used in the above reaction may be any one which does not exert an influence on the reaction, and examples thereof include ethers such as diethyl ether, tetrahydrofuran, dioxane, etc.; halogenated hydrocarbons such as methylene chloride, chloroform, dichloroethane, etc.; aromatic hydrocarbons such as benzene, toluene, etc.; and dimethylformamide.

Examples of the above tertiary amine include triethylamine, tributylamine, pyridine, 4-(dimethylamino)pyridine and the like.

The amount of the phosphorous acid triester is at least 2 mol, and preferably from 2 to 2.4 mol, per mol of the bishalogenomethylnaphthalene (81). The reaction is usually conducted at 80 to 150° C. and is completed within the range from about 1 to 4 hours.

Reaction scheme (IV)

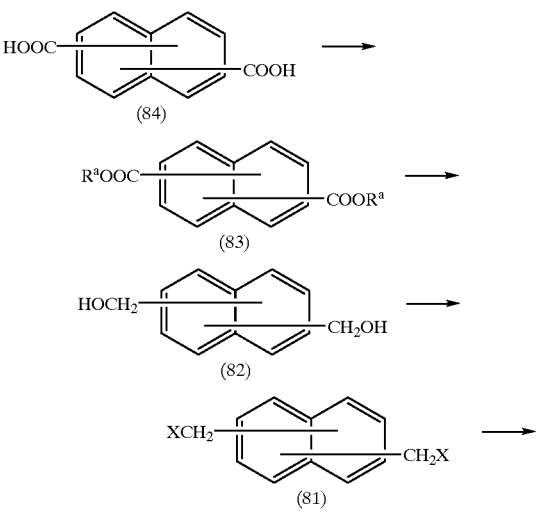

wherein $R^a$ represents an alkyl group having 1 to 6 carbon atoms and X is as defined above.

According to this reaction, a compound (81) as a starting material of the reaction scheme (III) is obtained by subjecting naphthalenedicarboxylic acid (84) to a normal esterification reaction to obtain an ester derivative (83) of naphthalenedicarboxylic acid, reducing this ester derivative (83) with a hydroreducing agent to obtain a bishydroxymethyl compound of naphthalene represented by the general formula (82), and reacting this compound (82) with a halogenating agent.

The above esterification reaction is conducted, for example, by reacting naphthalenedicarboxylic acid (84) with alcohols represented by the general formula (85):

$R^a$—OH wherein $R^a$ is as defined above, in the presence of a catalyst.

As the catalyst, a catalyst used conventionally in the esterification reaction is used, and specific examples thereof include inorganic acids such as hydrogen chloride, concentrated sulfuric acid, phosphoric acid, polyphosphoric acid, boron trifluoride, perchloric acid, etc.; organic acids such as trifluoroacetic acid, trichloromethanesulfonic acid, naphthalenesulfonic acid, p-toluenesulfonic acid, benzenesulfonic acid, ethanesulfonic acid, etc.; acid anhydrides such as trichloromethanesulfonic anhydride, trifluoromethanesulfonic anhydride, etc.; and thionyl chloride.

The above esterification reaction is conducted in the presence or absence of a proper solvent. As the catalyst, a catalyst used conventionally in the esterification reaction is used, and specific examples thereof include aromatic hydrocarbons such as benzene, toluene, xylene, etc.; halogenated hydrocarbons such as dichloromethane, dichloroethane, chloroform, etc.; and ethers such as diethyl ether, tetrahydrofuran, dioxane, etc.

The amount of the alcohols (85) is from 2 to 6 mol, and preferably from 3 to 4 mol, per mol of the compound (84). The reaction is usually conducted at 80 to 160° C., and preferably from 100 to 150° C.

The compound (83) can obtained by using a method of reacting an alkali metal salt (e.g. sodium salt potassium salt, etc.) of the compound (84) with alcohols (85) represented by the general formula (86):

Rᵃ—X wherein $R^a$ and X are as defined above, or a method of converting a carboxyl group of the compound (84) into a reactive group (e.g. acid chloride, amide or anhydride) using a condensing agent or a halogenating agent, and reacting with alcohols (85). These esterification reactions can be conducted by a conventional method.

The reaction used to obtain the compound (82) from the compound (83) is conducted in a proper solvent. Examples of the solvent include ethers such as diethyl ether, tetrahydrofuran, dioxane, diglyme, etc.; aliphatic hydrocarbons such as hexane, heptane, etc.; and aromatic hydrocarbons such as benzene, toluene, etc.

Examples of the hydroreducing agent used in this reaction include lithium aluminum hydride, aluminum hydride, diisopropylaluminum hydride, lithium boron hydride, sodium boron hydride-aluminum chloride, diboran and the like.

The amount of the hydroreducing agent is at least 2 mol, and preferably from 2 to 2.2 mol, per mol of the compound (83). The reaction is usually conducted at temperature under ice-cooling to 120° C., preferably from about 30 to 80° C., and is completed within the range from about 1 to 20 hours.

The reaction used to obtain the compound (81) from the compound (82) is conducted in the presence or absence of a proper solvent. Examples of the solvent include ethers such as diethyl ether, tetrahydrofuran, dioxane, etc.; halogenated hydrocarbons such as methylene chloride, chloroform, dichloroethane, etc.; and aromatic hydrocarbons such as benzene, toluene, etc.

Examples of the halogenating agent used in this reaction include thionyl halides such as thionyl chloride, thionyl bromide, etc.; hydrogen halides such as hydrogen chloride, hydrogen bromide, hydrogen iodide, etc.; and phosphorous halides such as phosphorous trichloride, phosphorous tribromide, etc.

The amount of the halogenating agent is at least 2 mol, and preferably from 2 to 3 mol, per mol of the compound (82). The reaction is usually conducted at temperature under ice-cooling to 120° C., preferably from about 40 to 100° C., and is completed within the range from about 1 to 18 hours.

The stilbene derivative wherein the groups $R^1$ and $R^3$ or $R^2$ and $R^4$ are different is synthesized by successively reacting a monophosphate derivative with a formyl compound (2) of triphenylamine having a different group in place of the above bisphosphate derivative (3).

Specifically, as shown in the following reaction scheme (V), a compound represented by the general formula (87) is first reacted with a phosphorous acid triester to obtain a monophosphate (88), and then the monophosphate is reacted with a formyl compound (2) of triphenylamine to obtain a monostilbene derivative, which is further halogenated to obtain a compound (90).

Reaction scheme (V)

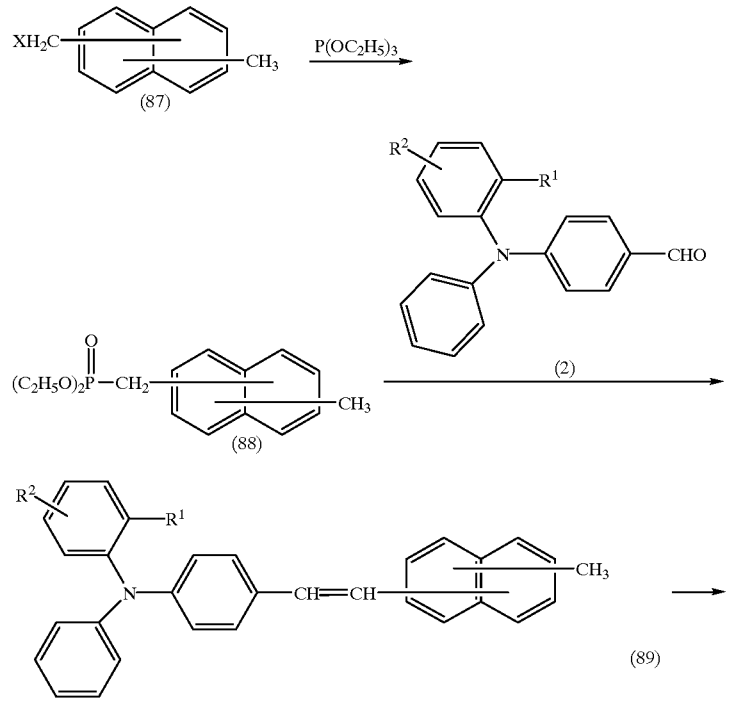

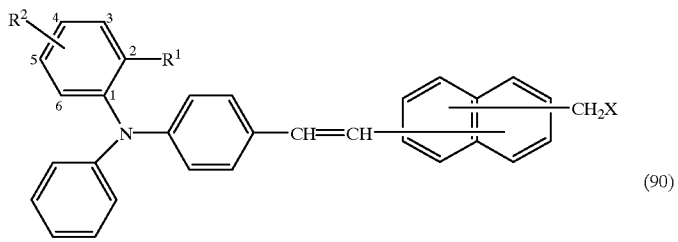

(90)

wherein $R^1$, $R^2$ and X are as defined above.

As shown in the following reaction scheme (VI), the above compound (90) is reacted with phosphorous acid triester to obtain a compound (91), and this compound is reacted with a formyl compound (2') of triphenylamine to obtain a stilbene derivative (1-b).

Reaction scheme (VI)

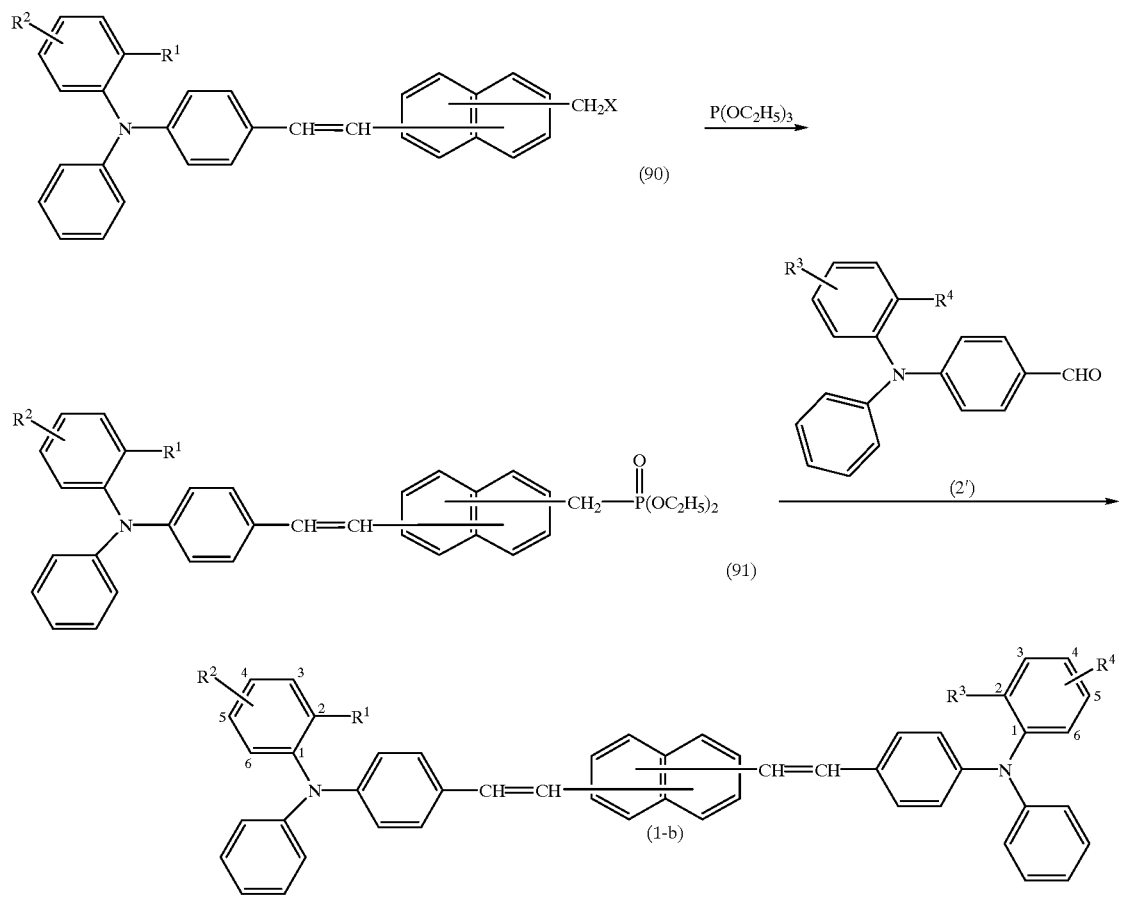

wherein $R^1$ to $R^4$ and X are as defined above.

The above compound (87) as a starting material of the reaction scheme (V) can be synthesized by successively subjecting to the esterification reaction, reducing reaction and halogenation reaction using methylnaphthalenecarboxylic acid (92) in place of naphthalenedicarboxylic acid (84) in the same manner as that described in the above reaction scheme (IV).

The stilbene derivative represented by the above general formula (1) can be suitably used as a hole transferring material in the electrophotosensitive material and can also be used in various fields such as solar battery, electroluminescence device and the like because of large electric charge mobility described above, that is, high hole transferring capability.

The electrophotosensitive material of the present invention will be described hereinafter.

The electrophotosensitive material of the present invention is that obtained by providing a photosensitive layer containing the stilbene derivative represented by the general formula (1) on a conductive substrate. The electrophotosensitive material includes a single-layer type and a multi-layer type, but the present invention can be applied to both of them.

The single-layer type electrophotosensitive material is that obtained by providing a single photosensitive layer on a conductive substrate. This photosensitive layer is formed by dissolving or dispersing a stilbene derivative (hole transferring material) represented by the general formula (1), an electric charge transferring material, a binding resin and, if necessary, an electron transferring material in a proper solvent, applying the resulting coating solution on a conductive substrate and drying the coating solution. Such a single-layer electrophotosensitive material can be applied to both positive charging and negative charging type in a single construction, and the productivity is excellent because of simple layer construction.

Regarding the single-layer type electrophotosensitive material of the present invention, the residual potential of the photosensitive material is considerably lowered and the sensitivity is improved in comparison with a conventional single-layer type electrophotosensitive material.

On the other hand, the multi-layer electrophotosensitive material is obtained by first providing an electric charge generating layer containing an electric charge generating material on a conductive substrate using a means such as deposition, application or the like, applying a coating solution containing at least one stilbene derivative (hole transferring material) represented by the general formula (1) and a binding resin on this electric charge generating layer, and drying the coating solution to form an electric charge transferring layer. To the contrary, the electric charge transferring layer may be formed on the conductive substrate and the electric charge generating layer may be formed thereon. Since the electric charge generating layer has a considerably smaller film thickness than that of the electric charge transferring layer, it is preferred that the electric charge generating layer is formed on the conductive substrate and the electric charge transferring layer is formed thereon in order to protect the electric charge generating layer.

The charging type (positive or negative) of the electrophotosensitive material is selected according to the order of formation of the above electric charge generating layer and electric charge transferring layer and the kind of the electric charge transferring material used in the electric charge transferring layer. For example, in case where the electric charge generating layer is formed on the conductive substrate and the electric charge transferring layer is formed thereon, as described above, and when the hole transferring material such as the stilbene derivative (1) of the present invention is used as the electric charge transferring material in the electric charge transferring layer, the resulting photosensitive material becomes a negative charging type.

Regarding the multi-layer type electrophotosensitive material of the present invention, the residual potential of the photosensitive material is considerably lowered and the sensitivity is improved in comparison with the multi-layer type electrophotosensitive material using a conventional derivative as the hole transferring material.

As described above, the electrophotosensitive material of the present invention can be applied to both of the single-layer type and multi-layer type. The single-layer type is preferred because of the following reason. That is, the single-layer type can be used in both (negative and positive) charging types and can be easily produced because of its simple structure. Furthermore, film failures can be inhibited at the time of formation of the film and the optical characteristics can be improved because of small interlaminar surface.

Various materials used in the electrophotosensitive material of the present invention will be described below.

Examples of the electric charge generating material used in the present invention include compounds represented by the following general formulas (CG1) to (CG12).

(CG1) Metal-Free Phthalocyanine

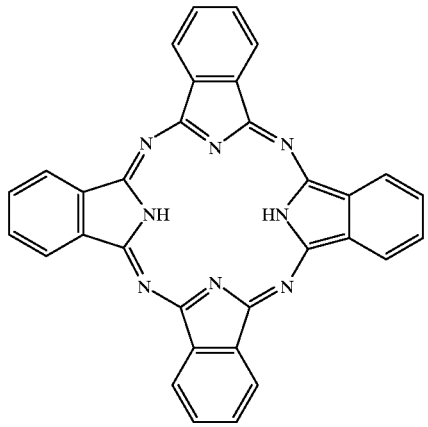

(CG1)

(CG2) Oxotitanyl phthalocyanine

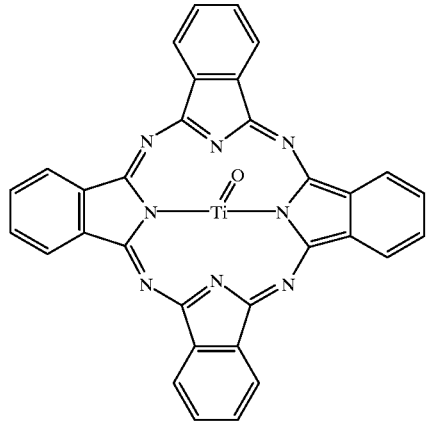

(CG2)

(CG3) Perylene pigment (CG3)

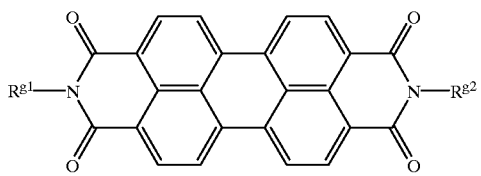

(wherein $R^{g1}$ and $R^{g2}$ are the same or different and represent a substituted or non-substituted alkyl group having 18 or less carbon atoms, a cycloalkyl group, an aryl group, an alkanoyl group or an aralkyl group)

(CG4) Bisazo Pigment $$Cp^1-N=N-Q-N=N-Cp^2 \quad (CG4)$$

[wherein $Cp^1$ and $Cp^2$ are the same or different and represent a coupler residue; and Q represents groups represented by the following formulas:

(Q-1)

(wherein $R^{g3}$ represents a hydrogen atom, an alkyl group, an aryl group or a heterocyclic group, and the alkyl group, aryl group or heterocyclic group may have a substituent; and ω represents 0 or 1), (Q-2)

(Q-3)

(wherein $R^{g4}$ and $R^{5g}$ are the same or different and represents a hydrogen atom, an alkyl group having 1 to 5 carbon atoms, a halogen atom, an alkoxy group, an aryl group or an aralkyl group), (Q-4)

(Q-5)

(Q-6)

(wherein $R^{g6}$ represents a hydrogen atom, an ethyl group, a chloroethyl group or a hydroxyethyl group), (Q-7)

or (Q-8)

(wherein $R^{g7}$, $R^{g8}$ and $R^{g9}$ are the same or different and represent a hydrogen atom, an alkyl group having 1 to 5 carbon atoms, a halogen atom, an alkoxy group, an aryl group or an aralkyl group)]

(CG5) Dithioketopyrrolopyrrole pigment (CG5)

(wherein $R^{g10}$ and $R^{g11}$ are the same or different and represent a hydrogen atom, an alkyl group, an alkoxy group or a halogen atom; and $R^{g12}$ and $R^{g13}$ are the same or different and represent a hydrogen atom, an alkyl group or an aryl group)

(CG6) Metal-free naphthalocyanine pigment (CG6)

(wherein $R^{g14}$, $R^{g15}$, $R^{g16}$ and $R^{g17}$ are the same or different and represent a hydrogen atom, an alkoxy group or a halogen atom)

(CG7) Metal phtalocyanine pigment

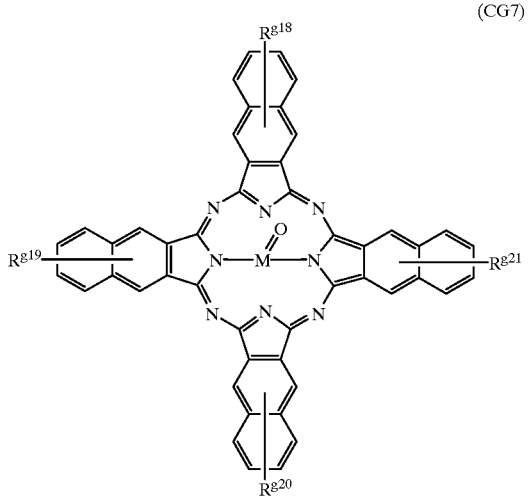

(wherein $R^{g18}$, $R^{g19}$, $R^{g20}$ and $R^{g21}$ are the same or different and represent a hydrogen atom, an alkyl group, an alkoxy group or a halogen atom; and M represents Ti or V)

(CG8) Squaline pigment

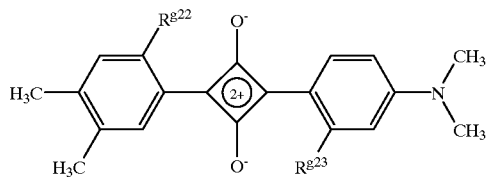

(wherein $R^{g22}$ and $R^{g23}$ are the same or different and represent a hydrogen atom, an alkyl group, an alkoxy group or a halogen atom)

(CG9) Trisazo pigment

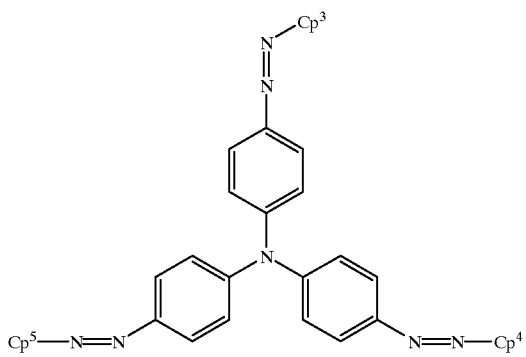

(wherein $Cp^3$, $Cp^4$ and $Cp^5$ are the same or different and represent a coupler residue)

(CG10) Indigo pigment

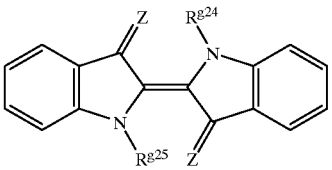

(wherein $R^{g24}$ and $R^{g25}$ are the same or different and represent a hydrogen atom, an alkyl group or an aryl group; and Z is an oxygen atom or a sulfur atom)

(CG11) Azulenium pigment

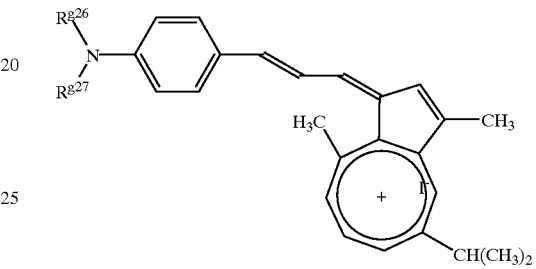

(wherein $R^{g26}$ and $R^{g27}$ are the same or different and represent a hydrogen atom, an alkyl group or an aryl group)

(CG12) Cyanine pigment

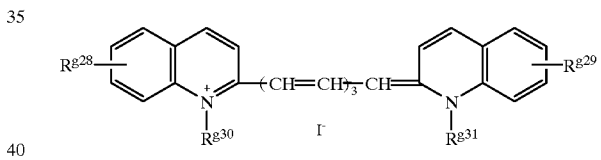

(wherein $R^{g28}$ and $R^{g29}$ are the same or different and represent a hydrogen atom, an alkyl group, an alkoxy group or a halogen atom; and $R^{g30}$ and $R^{g31}$ are the same or different and represent a hydrogen atom, an alkyl group or an aryl group).

In the above electric charge generating material, examples of the alkyl group include groups having 5 to 6 carbon atoms such as n-pentyl, n-hexyl and the like, in addition to the same groups as those described above. Examples of the substituted or non-substituted alkyl group having 18 or less carbon atoms include groups such as heptyl, octyl, nonyl, decyl, dodecyl, tridecyl, pentadecyl, octadecyl, etc., in addition to the alkyl groups having 1 to 6 carbon atoms.

Examples of the cycloalkyl group include groups having 3 to 8 carbon atoms such as cyclopropyl, cyclobutyl, cyclopentyl, cyclohexyl, cycloheptyl, cyclooctyl and the like.

Examples of the alkoxy group include groups having 1 to 6 carbon atoms such as methoxy, ethoxy, n-propoxy, isopropoxy, t-butoxy, n-pentyloxy, n-hexyloxy and the like.

Examples of the aryl group include groups such as phenyl, napthyl, anthryl, phenanthryl and the like. Examples of the alkanoyl group include formyl, acetyl, propionyl, butyryl, pentanoyl, hexanoyl and the like. Examples of the halogen atom include fluorine, chlorine, bromine, iodine and the like.

Examples of the heterocyclic group include thienyl, furyl, pyrrolyl, pyrrolidinyl, oxazolyl, isoxazolyl, thiazolyl, isothiazolyl, imidazolyl, 2H-imidazoyl, pyrazolyl, triazolyl, tetrazolyl, pyranyl, pyridyl, piperidyl, piperidino, 3-morpholinyl, morpholino, thiazolyl and the like. The heterocyclic group may also be ones condensed with an aromatic ring.

Examples of the substituent which may be substituted on the above groups include halogen atom, amino group, hydroxyl group, optionally esterified carboxyl group, cyano group, alkyl group having 1 to 6 carbon atoms, alkoxy group having 1 to 6 carbon atoms, alkenyl group having 2 to 6 carbon atoms which may have an aryl group and the like.

Examples of the coupler residue represented by $Cp^1$, $Cp^2$, $Cp^3$, $Cp^4$ and $Cp^5$ include the groups shown in the following general formulas (Cp-1) to (Cp-11).

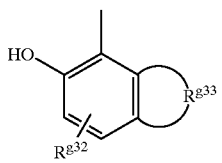
(Cp-1)

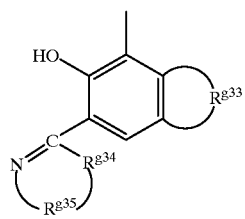
(Cp-2)

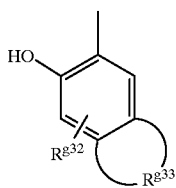
(Cp-3)

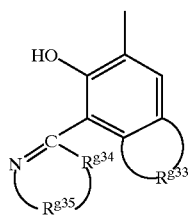
(Cp-4)

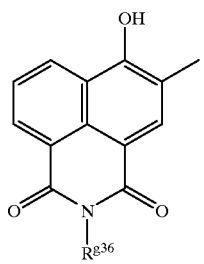
(Cp-5)

-continued

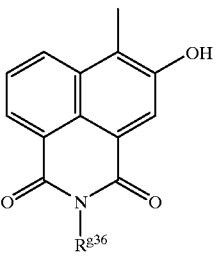
(Cp-6)

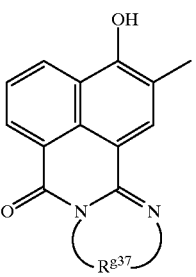
(Cp-7)

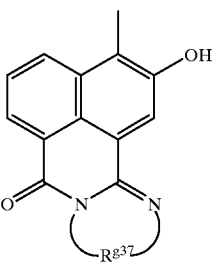
(Cp-8)

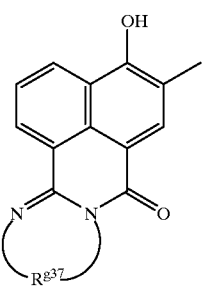
(Cp-9)

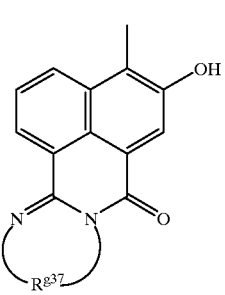
(Cp-10)

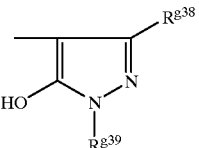
(Cp-11)

In the respective formulas, $R^{g32}$ is a carbamoyl group, a sulfamoyl group, an allophanoyl group, oxamoyl group, anthraniloyl group, carbazoyl group, glycyl group, hydantoyl group, phthalamoyl group or a succinamoyl group. These groups may have substituents such as halogen atom, phenyl group which may have a substituent, naphthyl group which may have a substituent, nitro group, cyano group, alkyl group, alkenyl group, carbonyl group, carboxyl group and the like.

$R^{g33}$ is an atomic group which is required to form an aromatic ring, a polycyclic hydrocarbon or a heterocycle by condensing with a benzene ring. These rings may have the same substituent as that described above.

$R^{g34}$ is an oxygen atom, a sulfur atom or an imino group.

$R^{g35}$ is a divalent chain hydrocarbon or an aromatic hydrocarbon group, and these groups may have the same substituent as that described above.

$R^{g36}$ is an alkyl group, an aralkyl group, an aryl group or a heterocyclic group. These groups may have the same substituent as that described above.

$R^{g37}$ is an atomic group which is required to form a heterocycle together with a divalent chain hydrocarbon or aromatic hydrocarbon group or two nitrogen atoms in the above formulas (Cp-1) to (Cp-2). These rings may have the same substituent as that described above.

$R^{g38}$ is a hydrogen atom, an alkyl group, an amino group, a carbamoyl group, a sulfamoyl group, an allophanoyl group, a carboxyl group, an alkoxycarbonyl group, an aryl group or a cyano group. The groups other than a hydrogen atom may have the same substituent as that described above.

$R^{g39}$ is an alkyl group or an aryl group which may have the same substituent as that described above.

Examples of the alkenyl group include alkenyl groups having 2 to 6 carbon atoms such as vinyl, allyl, 2-butenyl, 3-butenyl, 1-methylallyl, 2-pentenyl, 2-hexenyl and the like.

In the above $R^{g33}$, examples of the atomic group which is required to form an aromatic ring by condensing with a benzene ring include alkylene groups having 1 to 4 carbon atoms such as methylene, ethylene, trimethylene, tetramethylene and the like.

Examples of the aromatic ring to be formed by condensing the above $R^{g33}$ with a benzene ring include naphthalene ring, anthracene ring, phenanthrene ring, pyrene ring, chrysene ring, naphthacene ring and the like.

In the above $R^{g33}$, examples of the atomic group which is required to form a polycyclic hydrocarbon by condensing with a benzene ring include the above alkylene groups having 1 to 4 carbon atoms, carbazole ring, benzocarbazole ring, dibenzofuran ring and the like.

In the above $R^{g33}$, examples of the atomic group which is required to form a heterocycle by condensing with a benzene ring include benzofuranyl, benzothiophenyl, indolyl, benzoxazolyl, 1H-indolyl, benzothiazolyl, 1H-indadolyl, benzoimidazolyl, chromenyl, chromanyl, isochromanyl, quinolinyl, isoquinolinyl, cinnolinyl, phthalazinyl, quinazolinyl, quinoxalinyl, dibenzofranyl, acarbazoyl, xanthenyl, acridinyl, phenanthridinyl, phenazinyl, phenoxazinyl, thianthrenyl and the like.

Examples of the aromatic heterocyclic group to be formed by condensing the above $R^{g33}$ and the benzene ring include thienyl, furyl, pyrrolyl, oxazolyl, isoxazolyl, thiazolyl, isothiazolyl, imidazolyl, pyrazolyl, triazolyl, tetrazolyl, pyridyl, thiazolyl and the like. In addition, it may also be a heterocyclic group condensed with other aromatic rings (e.g. benzofuranyl, benzoimidazolyl, benzoxazolyl, benzothiazolyl, quinolyl, etc.).

In the above $R^{g35}$ and $R^{g37}$, examples of the divalent chain hydrocarbon include ethylene, trimethylene, tetramethylene and the like. Examples of the divalent aromatic hydrocarbon include phenylene, naphthylene, phenanthrilene and the like.

In the above $R^{g36}$, examples of the heterocyclic group include pyridyl, pyrazyl, thienyl, pyranyl, indolyl and the like.

In the above $R^{g37}$, examples of the atomic group which is required to form a heterocycle together with two nitrogen atoms include phenylene, naphthylene, phenanthrylene, ethylene, trimethylene, tetramethylene and the like.

Examples of the aromatic heterocyclic group to be formed by the above $R^{g37}$ and two nitrogen atoms include benzoimidazole, benzo[f]benzoimidazole, dibenzo[e,g] benzoimidazole, benzopyrimidine and the like. These groups may have the same substituent as that described above.

In the above $R^{g38}$, examples of the alkoxycarbonyl group include groups such as methoxycarbonyl, ethoxycarbonyl, propoxycarbonyl, butoxycarbonyl and the like.

In the present invention, there can be used powders of inorganic photoconductive materials such as selenium, selenium—tellurium, selenium—arsenic, cadmium sulfide, amorphous silicon, etc. and known electric charge generating materials such as pyrilium salt, anthanthrone pigments, triphenylmethane pigments, threne pigments, toluidine pigments, pyrazoline pigments, quinacridone pigments, etc. in addition to the above electric charge generating materials.

The above electric charge generating materials can be used alone or in combination thereof to present an absorption wavelength within a desired range.

A photosensitive material having sensitivity at the wavelength range of 700 nm or more is required in digital-optical image forming apparatuses such as laser beam printer using a light source of semiconductor laser, facsimile and the like. Therefore, among the above electric charge generating materials, phthalocyanine pigments such as metal-free phthalocyanine represented by the above general formula (CG1), oxotitanyl phthalocyanine represented by the general formula (CG2) and the like are preferably used. The crystal form of the above phthalocyanine pigments is not specifically limited, and various phthalocyanine pigments having different crystal form can be used.

In analogue-optical image forming devices such as electrostatic-copying machine using a white light source such as halogen lamp, etc., a photosensitive material having sensitivity at the visible range is required. Therefore, the perylene pigment represented by the above general formula (CG3) and bisazo pigment represented by the general formula (CG4) and the like are suitably used.

Hole Transferring Material

In the electrophotosensitive material of the present invention, a stilbene derivative (1) as the hole transferring material and other known hole transferring materials may be contained in the photosensitive layer.

Examples of the hole transferring material include various compounds having high hole transferring capability, for example, compounds represented by the following general formulas (HT1) to (HT13):

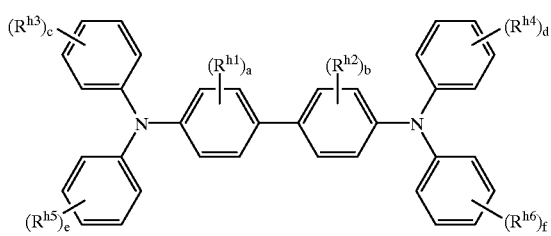

(HT1)

(wherein $R^{h1}$, $R^{h2}$, $R^{h3}$, $R^{h4}$, $R^{h5}$ and $R^{h6}$ are the same or different and represent a halogen atom, an alkyl group which may have a substituent, an alkoxy group which may have a substituent or an aryl group which may have a substituent; a and b are the same or different and represent an integer of 0 to 4; c, d, e and f are the same or different and represent an integer of 0 to 5; and each $R^{h1}$, $R^{h2}$, $R^{h3}$, $R^{h4}$, $R^{h5}$ and $R^{h6}$ may be different provided that a, b, c, d, e or f is 2 or more)

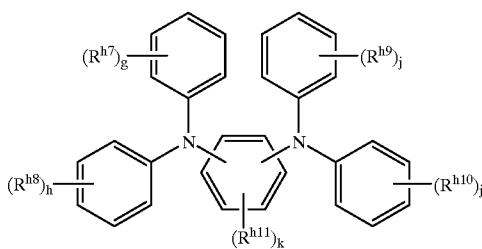

(HT2)

(wherein $R^{h7}$, $R^{h8}$, $R^{h9}$, $R^{h10}$ and $R^{h11}$ are the same or different and represent a halogen atom, an alkyl group which may have a substituent, an alkoxy group which may have a substituent or an aryl group which may have a substituent; g, h, i and j are the same or different and represent an integer of 0 to 5; k represents an integer of 0 to 4; and each $R^{h7}$, $R^{h8}$, $R^{h9}$, $R^{h10}$ and $R^{h11}$ may be different provided that g, h, i, j or k is 2 or more)

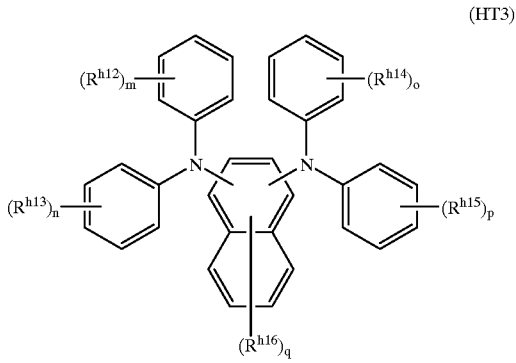

(HT3)

(wherein $R^{h12}$, $R^{h13}$, $R^{h14}$ and $R^{h15}$ are the same or different and represent a halogen atom, an alkyl group which may have a substituent, an alkoxy group which may have a substituent or an aryl group which may have a substituent; $R^{h16}$ is a halogen atom, a cyano group, a nitro group, an alkyl group which may have a substituent, an alkoxy which may have a substituent or aryl group which may have a substituent; m, n, o and p are the same or different and represent an integer of 0 to 5; and q is an integer of 0 to 6; each $R^{h12}$, $R^{h13}$, $R^{h14}$, $R^{h15}$ and $R^{h16}$ may be different provided that m, n, o, p or q is 2 or more)

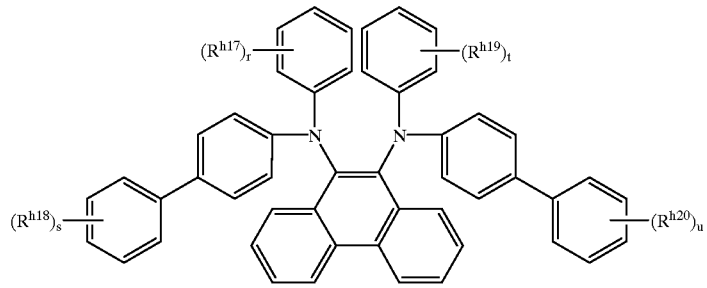

(HT4)

(wherein $R^{h17}$, $R^{h18}$, $R^{h19}$ and $R^{h20}$ are the same or different and represent a halogen atom, an alkyl group which may have a substituent, an alkoxy group which may have a substituent or an aryl group which may have a substituent; r, s, t and u are the same or different and represent an integer of 0 to 5; and that each $R^{h17}$, $R^{h18}$, $R^{h19}$ and $R^{h20}$ may be different provided that r, s, t or u is 2 or more)

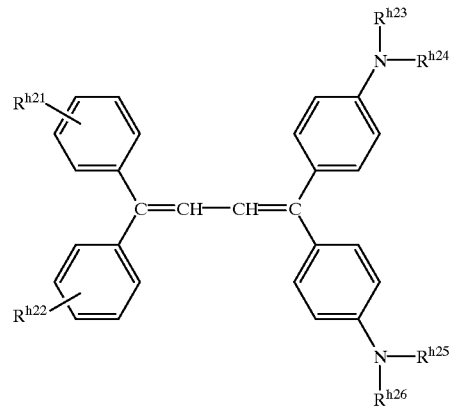

(HT5)

(wherein $R^{h21}$ and $R^{h22}$ are the same or different and represent a hydrogen atom, a halogen atom, an alkyl group or an alkoxy group, and $R^{h23}$, $R^{h24}$, $R^{h25}$ and $R^{h26}$ may be the same or different and represent a hydrogen atom, an alkyl group or an aryl group)

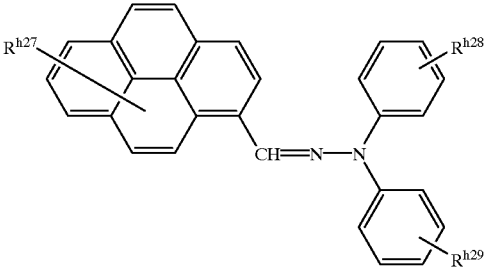

(HT6)

(wherein $R^{h27}$, $R^{h28}$ and $R^{h29}$ are the same or different and represent a hydrogen atom, a halogen atom, an alkyl group or an alkoxy group)

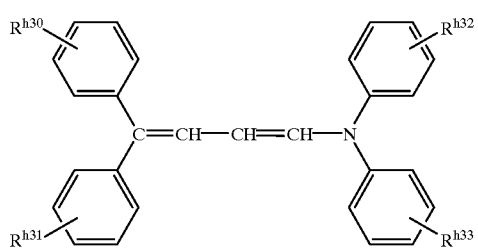

(HT7)

(wherein $R^{h30}$, $R^{h31}$, $R^{h32}$ and $R^{h33}$ may be the same or different and represent a hydrogen atom, a halogen atom, an alkyl group or an alkoxy group)

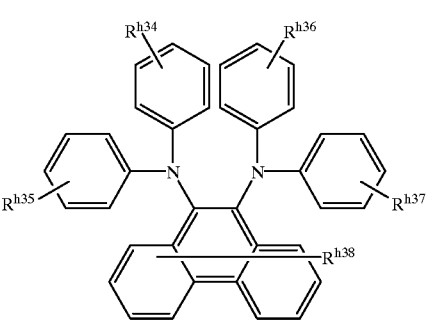

(HT8)

(wherein $R^{h34}$, $R^{h35}$, $R^{h36}$, $R^{h37}$ and $R^{h38}$ may be the same or different and represent a hydrogen atom, a halogen atom, an alkyl group or an alkoxy group)

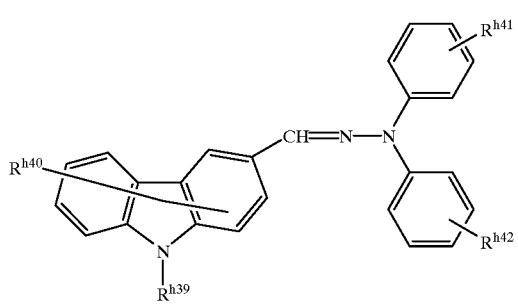

(HT9)

(wherein $R^{h39}$ is a hydrogen atom or an alkyl group, and $R^{h40}$, $R^{h41}$ and $R^{h42}$ may be the same or different and represent a hydrogen atom, a halogen atom, an alkyl group or an alkoxy group)

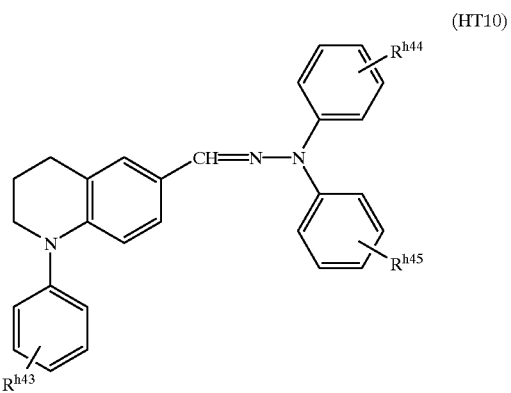

(HT10)

(wherein $R^{h43}$, $R^{h44}$ and $R^{h45}$ may be the same or different and represent a hydrogen atom, a halogen atom, an alkyl group or an alkoxy group)

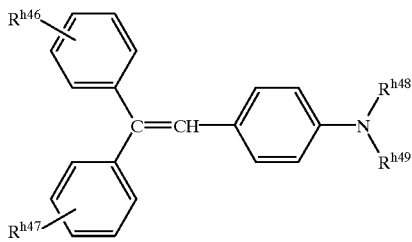

(HT11)

(wherein $R^{h46}$ and $R^{h47}$ are the same or different and represent a hydrogen atom, a halogen atom, an alkyl group which may have a substituent or an alkoxy group which may have a substituent; and $R^{h48}$ and $R^{h49}$ are the same or different and represent a hydrogen atom, an alkyl group which may have a substituent, or an aryl group which may have a substituent)

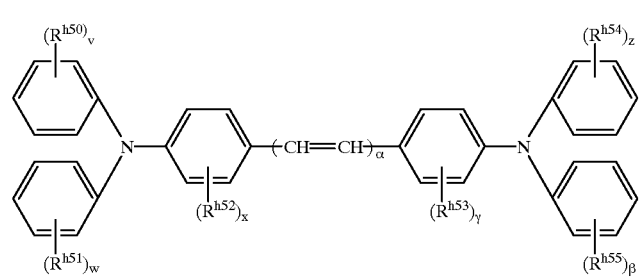

(HT12)

(wherein $R^{h50}$, $R^{h51}$, $R^{h52}$, $R^{h53}$, $R^{h54}$ and $R^{h55}$ are the same or different and represent an alkyl group which may have a substituent, an alkoxy group which may have a substituent or an aryl group which may have a substituent; α is an integer of 1 to 10; v, w, x, y, z and β are the same or different and represent an integer of 0 to 2; and each $R^{h50}$, $R^{h51}$, $R^{h52}$, $R^{h53}$, $R^{h54}$ and $R^{h55}$ may be different provided that v, w, x, y, z or β is 2)

(HT13)

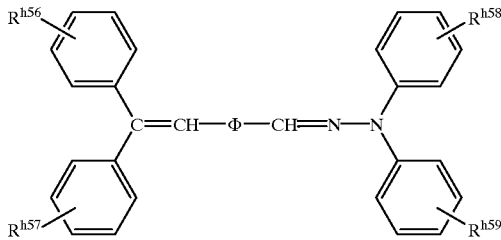

(wherein $R^{h56}$, $R^{h57}$, $R^{h58}$ and $R^{h59}$ may be the same or different and represent a hydrogen atom, a halogen atom, an alkyl group or an alkoxy group, and Φ represent a group represented by the formulas (Φ-1), (Φ-2) or (Φ-3):

(Φ-1)

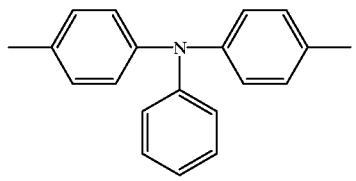

(Φ-2)

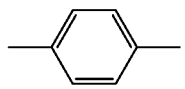

(Φ-3)

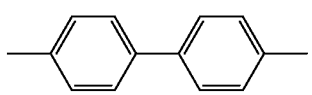

In the hole transferring material described above, examples of the alkyl group, alkoxy group, aryl group, aralkyl group and halogen atom include the same groups as those described above.

Examples of the substituent which may be substituted on the above groups include halogen atom, amino group, hydroxyl group, optionally esterified carboxyl group, cyano group, alkyl group having 1 to 6 carbon atoms, alkoxy group having 1 to 6 carbon atoms, alkenyl group having 2 to 6 carbon atoms which may have an aryl group, etc. The substitution position of the substituent is not specifically limited.

In the present invention, there can be used hole transferring materials which have hitherto been known, that is, nitrogen-containing cyclic compounds and condensed polycyclic compounds, e.g. oxadiazole compounds such as 2,5-di(4-methylaminophenyl)-1,3,4-oxadiazole, etc.; styryl compounds such as 9-(4-diethylaminostyryl)anthracene, etc.; carbazole compounds such as polyvinyl carbazole, etc.; organopolysilane compounds; pyrazoline compounds such as 1-phenyl-3-(p-dimethylaminophenyl)pyrazoline, etc.; hydrazone compounds; triphenylamine compounds; indole compounds; oxazole compounds; isoxazole compounds; thiazole compounds; thiadiazole compounds; imidazole compounds; pyrazole compounds; and triazole compounds, together with or in place of the above hole transferring materials (HT-1) to (HT-13).

In the present invention, these hole transferring materials may be used alone or in combination thereof. When using the hole transferring material having film forming properties, such as poly(vinylcarbazole), etc., a binding resin is not required necessarily.

Electron Transferring Material

Examples of the electron transferring materials include various compounds having high electron transferring capability, for example, compounds represented by the following general formulas (ET1) to (ET17):

(ET1)

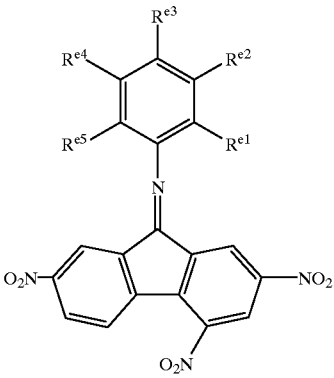

(wherein $R^{e1}$, $R^{e2}$, $R^{e3}$, $R^{e4}$ and $R^{e5}$ are the same or different and represent a hydrogen atom, an alkyl group which may have a substituent, an alkoxy group which may have a substituent, an aryl group which may have a substituent, an aralkyl group which may have a substituent, a phenoxy group which may have a substituent or a halogen atom)

(ET2)

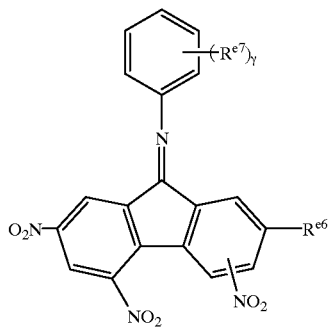

(wherein $R^{e6}$ represents an alkyl group; $R^{e7}$ represents an alkyl group which may have a substituent, an alkoxy group which may have a substituent, an aryl group which may have a substituent, an aralkyl group which may have a substituent, a halogen atom or a halogenated alkyl group; γ represents an integer of 0 to 5; and each $R^{e7}$ may be different provided that γ is 2 or more)

(ET3)

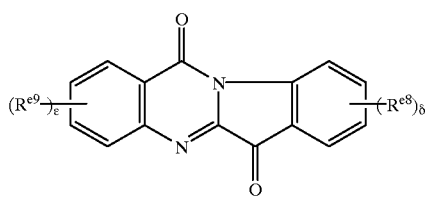

(wherein $R^{e8}$ and $R^{e9}$ may be the same or different and represent an alkyl group; δ represents an integer of 1 to 4; ε represents an integer of 0 to 4; and each $R^{e8}$ and $R^{e9}$ may be different provided that δ and ε are 2 or more)

(ET4)

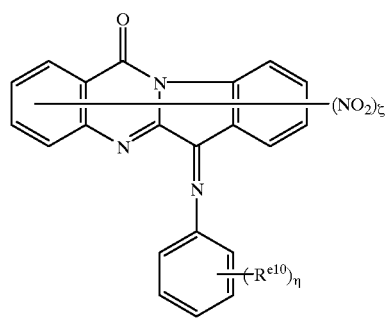

(wherein $R^{e10}$ represents an alkyl group, an aryl group, an aralkyl group, an alkoxy group, a halogenated alkyl group or a halogen atom; ζ represents an integer of 0 to 4; ƒ represents an integer of 0 to 5; and each $R^{e10}$ may be different provided that ƒ is 2 or more)

(ET5)

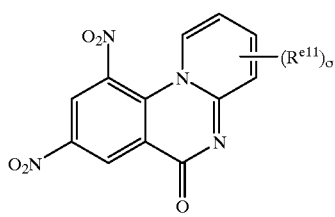

(wherein $R^{e11}$ represents an alkyl group; ∂ represents an integer of 1 to 4; and each $R^{ell}$ may be different provided that ∂ is 2 or more)

(ET6)

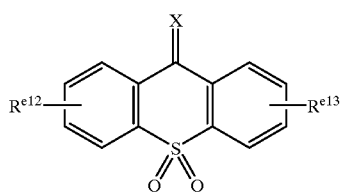

(wherein $R^{e12}$ and $R^{e13}$ are the same or different and represent a hydrogen atom, a halogen atom, an alkyl group, an aryl group, an aralkyloxycarbonyl group, an alkoxy group, a hydroxyl group, a nitro group or a cyano group; and X represents an oxygen atom, a =N—CN group or a =C(CN)$_2$ group)

(ET7)

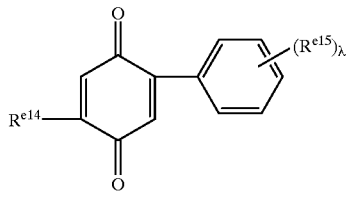

(wherein $R^{e14}$ represents a hydrogen atom, a halogen atom, an alkyl group or a phenyl group which may have a substituent; $R^{e15}$ represents a halogen atom, an alkyl group which may have a substituent, a phenyl group which may have a substituent, an alkoxycarbonyl group, a N-alkylcarbamoyl group, a cyano group or a nitro group; λ represents an integer of 0 to 3; and each $R^{e15}$ may be different provided that λ is 2 or more)

(ET8)

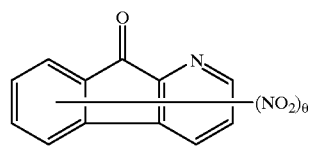

(wherein θ represents an integer of 1 to 2)

(ET9)

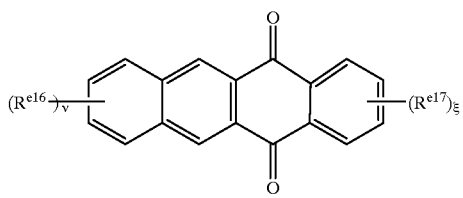

(wherein $R^{e16}$ and $R^{e17}$ are the same or different and represent a halogen atom, an alkyl group which may have a substituent, a cyano group, a nitro group or an alkoxycarbonyl group; and ν and ξ represent an integer of 0 to 3; and $R^{e16}$ and $R^{e17}$ may be different provided when ν or ξ is 2 or more)

(ET10)

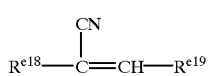

(wherein $R^{e18}$ and $R^{e19}$ are the same or different and represent a phenyl group, a polycyclic aromatic group or a heterocyclic group, and these groups may have a substituent)

(ET11)

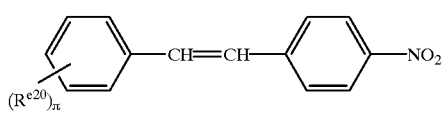

(wherein $R^{e20}$ represents an amino group, a dialkylamino group, an alkoxy group, an alkyl group or a phenyl group;

Π represents an integer of 1 to 2; and each $R^{e20}$ may be different provided that Π is 2)

(ET12)

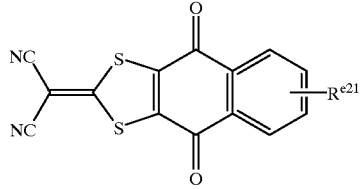

(wherein $R^{e21}$ represents a hydrogen atom, an alkyl group, an aryl group, an alkoxy group or an aralkyl group)

(ET13)

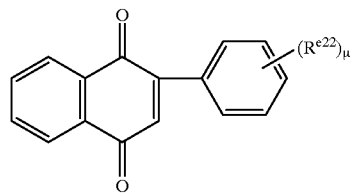

(wherein $R^{e22}$ represents a halogen atom, an alkyl group which may have a substituent, a phenyl group which may have a substituent, an alkoxycarbonyl group, a N-alkylcarbamoyl group, a cyano group or a nitro group; $\mu$ represents an integer of 0 to 3; and each $R^{e22}$ may be different provided that $\mu$ is 2 or more)

(ET14)

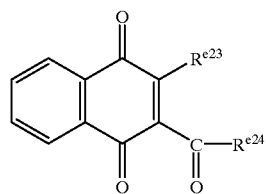

[wherein $R^{e23}$ represents an alkyl group which may have a substituent or an aryl group which may have a substituent; and $R^{e24}$ represents an alkyl group which may have a substituent, an aryl which may have a substituent, or a group: —O—$R^{e24a}$ ($R^{e24a}$ represents an alkyl group which may have a substituent, or an aryl group which may have a substituent)]

(ET15)

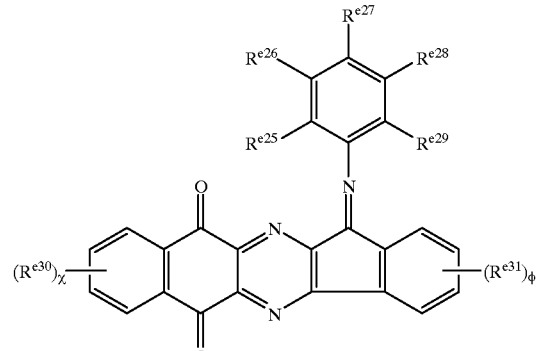

(wherein $R^{e25}$, $R^{e26}$, $R^{e27}$, $R^{e28}$, $R^{e29}$, $R^{e30}$ and $R^{e31}$ are the same or different and represent an alkyl group, aryl group, aralkyl group, alkoxy group, a halogen atom or a halogenated alkyl group; and × and φ are the same or different and represent an integer of 0 to 4)

(ET16)

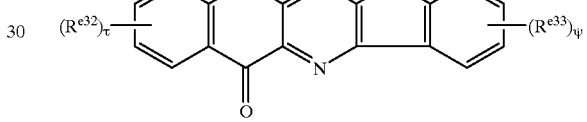

(wherein $R^{e32}$ and $R^{e33}$ are the same or different and represent an alkyl group, an aryl group, an alkoxy group, a halogen atom or a halogenated alkyl group; and τ and ψ are the same or different and represent an integer of 0 to 4)

(ET17)

(wherein $R^{e34}$, $R^{e35}$, $R^{e36}$ and $R^{e37}$ are the same or different and represent a hydrogen atom, an alkyl group, alkoxy group, an aryl group, an aralkyl group, a cycloalkyl group or an amino group provided that at least two substituents of $R^{e34}$, $R^{e35}$, $R^{e36}$ and $R^{e37}$ are the same groups other than hydrogen atom).

In the above electron transferring materials, examples of the alkyl group, alkoxy group, aryl group, aralkyl group, cycloalkyl group, alkoxycarbonyl group, heterocyclic group and halogen atom include the same groups as those described above.

Examples of the alkyl group and halogen atom in the halogenated alkyl group include the same groups as those described above.

Examples of the condensed polycyclic group include naphthyl, penanthryl and anthryl and the like. Examples of the aralkyloxycarbonyl group include those of which aralkyl portions are various aralkyl groups described above. Examples of the N-alkylcarbamoyl group include those of which alkyl portions are various alkyl groups described above.

Examples of the dialkylamino group include those of which alkyl portions are various alkyl groups described above. Two alkyl groups substituted on the amino may be the same or different.

Examples of the substituent, which may be substituted on each group described above, include halogen atom, amino group, hydroxyl group, optionally esterified carboxyl group, cyano group, alkyl group having 1 to 6 carbon atoms, alkoxy group having 1 to 6 carbon atoms, alkenyl group having 2 to 6 carbon atoms which may have an aryl group and the like. The substitution position of the substituent is not specifically limited.

In the present invention, there can be used known electron transferring materials such as benzoquinone compound, malononitrile compound, thiopyran compound, tetracyanoethylene, 2,4,8-trinitrothioxanthone, dinitrobenzene, dinitroanthracene, dinitroacridine, nitroanthraquinone, dinitroanthraquinone, succinic anhydride, maleic anhydride, dibromomaleic anhydride, etc., in addition to those described above.

In the present invention, these electron transferring materials may be used alone or in combination thereof.

Binding Resin

As the binding resin for dispersing the above respective components, there can be used various resins which have hitherto been used in the photosensitive layer, and examples thereof include thermoplastic resins such as styrene-butadiene copolymer, styrene-acrylonitrile copolymer, styrene-maleic acid copolymer, acrylic copolymer, styrene-acrylic acid copolymer, polyethylene, ethylene-vinyl acetate copolymer, chlorinated polyethylene, polyvinyl chloride, polypropylene, ionomer, vinyl chloride-vinyl acetate copolymer, polyester, alkyd resin, polyamide, polyurethane, polycarbonate, polyarylate, polysulfon, diaryl phthalate resin, ketone resin, polyvinyl butyral resin, polyether resin, polyester resin and the like; crosslinking thermosetting resins such as silicone resin, epoxy resin, phenol resin, urea resin, melamine resin and the like; and photosetting resins such as epoxy acrylate, urethane acrylate and the like.

In addition to the above respective components, various additives which have hitherto been known, such as deterioration inhibitors (e.g. antioxidants, radical scavengers, singlet quenchers, ultraviolet absorbers, etc.), softeners, plasticizers, surface modifiers, bulking agents, thickening agents, dispersion stabilizers, wax, acceptors, donors and the like can be formulated in the photosensitive layer as long as the electrophotographic characteristics are not adversely effected by the additives. In order to improve the sensitivity of the photosensitive layer, known sensitizers such as terphenyl, halonaphthoquinones, acenaphthylene and the like may be used in combination with the electric charge generating material.

In the single-layer type photosensitive material, the electric charge generating material is formulated in the amount of 0.1 to 50 parts by weight, and preferably 0.5 to 30 parts by weight, based on 100 parts by weight of the binding resin. The stilbene derivative (1) (hole transferring material) of the present invention is formulated in the amount of 20 to 500 parts by weight, and preferably 30 to 200 parts by weight, based on 100 parts by weight of the binding resin. When the electron transferring material is contained, it is suitable that the amount of the electron transferring material is from 5 to 100 parts by weight, and preferably from 10 to 80 parts by weight, based on 100 parts by weight of the binding resin. The thickness of the photosensitive layer in the single-layer type photosensitive material is from 5 to 100 $\mu$m, and preferably from 10 to 50 $\mu$m.

The electric charge generating material and binding resin, which constitute the electric charge generating layer, may be used in various proportions in the multi-layer photosensitive material. It is suitable that the electric charge generating material is formulated in the amount of 5 to 1,000 parts by weight, and preferably 30 to 500 parts by weight, based on 100 parts by weight of the binding resin. When a hole transferring material is contained in the electric charge generating layer, it is suitable that the hole transferring material is formulated in the amount of 10 to 500 parts by weight, and preferably 50 to 200 parts by weight, based on 100 parts by weight of the binding resin.

The hole transferring material and binding resin, which constitute the electric charge transferring layer, can be used in various proportions within such a range as not to prevent the transfer of electrons and to prevent the crystallization. It is suitable that the stilbene derivative (1) (hole transferring material) of the present invention is used in the amount of 10 to 500 parts by weight, and preferably 25 to 200 parts by weight, based on 100 parts by weight of the binding resin so as to easily transfer electric charges generated by light irradiation in the electric charge generating layer. When the electron transferring material is contained in the electric charge transferring layer, it is suitable that the electron transferring material is formulated in the amount of 5 to 200 parts by weight, and preferably 10 to 100 parts by weight, based on 100 parts by weight of the binding resin.

Regarding the thickness of the photosensitive layer in the multi-layer type photosensitive layer, the thickness of the electric charge generating layer is from about 0.01 to 5 $\mu$m, and preferably from about 0.1 to 3 $\mu$m, and that of the electric charge transferring layer is from 2 to 100 $\mu$m, and preferably from about 5 to 50 $\mu$m.

A barrier layer may be formed in such a range as not to injure the characteristics of the photosensitive material between the conductive substrate and photosensitive layer in the single-layer type photosensitive material, and between the conductive substrate and electric charge generating layer, between the conductive substrate layer and electric charge transferring layer or between the electric charge generating layer and electric charge transferring layer in the multi-layer type photosensitive material. Further, a protective layer may be formed on the surface of the photosensitive layer.

As the conductive substrate to be used in the electrophotosensitive material of the present invention, various materials having the conductivity can be used. Examples of the conductive substrate include single metals such as iron, aluminum, copper, tin, platinum, silver, vanadium, molybdenum, chromium, cadmium, titanium, nickel, palladium, indium, stainless steel, brass and the like; plastic materials which are vapor-deposited or laminated with the above metal; glass materials coated with aluminum iodide, tin oxide, indium oxide and the like.

The conductive substrate may be made in a form of a sheet or a drum according to a structure of the image forming device to be used. The substrate itself may have a conductivity or only the surface of the substrate may have a conductivity. It is preferred that the conductive substrate has sufficient mechanical strength when used.

When the above photosensitive layer is formed by the application method, the above electric charge generating material, electric charge transferring material and binding resin may be dispersed and mixed together with a suitable solvent by using a known method such as a roll mill, a ball mill, an atriter, a paint shaker, a supersonic dispenser, etc. to prepare a dispersion which is applied by using a known means and then allowed to dry.

As the solvent for preparing the coating solution, there can be used various organic solvents, and examples thereof include alcohols such as methanol, ethanol, isopropanol, butanol and the like; aliphatic hydrocarbons such as n-hexane, octane, cyclohexane and the like; aromatic hydrocarbons such as benzene, toluene, xylene and the like; halogenated hydrocarbons such as dichloromethane, dichloroethane, chloroform, carbon tetrachloride, chlorobenzene and the like; ethers such as dimethyl ether, diethyl ether, tetrahydrofuran, ethylene glycol dimethyl ether, diethylene glycol dimethyl ether and the like; ketones such as acetone, methyl ethyl ketone, cyclohexanone and the like; esters such as ethyl acetate, methyl acetate and the like; dimethylformaldehyde, dimethylformamide, dimethyl sulfoxide, and the like. These solvents may be used alone or in combination thereof.

In order to improve the dispersibility of the electric charge transferring material and electric charge generating material as well as the smoothness of the surface of the photosensitive layer, there may be used surfactants, leveling agents or the like.

EXAMPLES

The following Synthesis Examples, Examples and Comparative Examples further illustrate the present invention in detail.

Synthesis of Stilbene Derivative

Reference Example 1

Synthesis of 2,6-dimethyltriphenylamine 2,6-dimethylaniline (15 g, 124 mmol), iodobenzene (50 g, 245 mmol), andhyrous potassium carbonate (17 g, 123 mmol) and powdered copper (1 g, 16 mmol) were added in 150 ml of nitrobenzene, and the mixture was reacted under reflux for about 24 hours. After the completion of the reaction, the inorganic salt was removed and the solvent was distilled off. The resulting residue was purified by silica gel column chromatography (developing solvent: chloroform-hexane mixed solvent) to obtain 28.8 g of the titled compound (yield: 85%).

Reference Example 2

Synthesis of 2-ethyl-6-methyltriphenylamine

According to the same manner as that described in Reference Example 1 except for using an equimolar amount of 6-ethyl-o-toluidine in place of 2,6-dimethylaniline, the reaction was conducted to obtain 28.1 g of the titled compound (yield: 79%).

Reference Example 3

Synthesis of 2,6-diethyltriphenylamine

According to the same manner as that described in Reference Example 1 except for using an equimolar amount of 2,6-diethylaniline in place of 2,6-dimethylaniline, the reaction was conducted to obtain 31.0 g of the titled compound (yield: 83%).

Reference Example 4

Synthesis of 2,3-dimethyltriphenylamine

According to the same manner as that described in Reference Example 1 except for using an equimolar amount of 2,3-dimethylaniline in place of 2,6-dimethylaniline, the reaction was conducted to obtain 28.4 g of the titled compound (yield: 84%).

Reference Example 5

Synthesis of 2-ethyltriphenylamine

According to the same manner as that described in Reference Example 1 except for using an equimolar amount of 2-ethylaniline in place of 2,6-dimethylaniline, the reaction was conducted to obtain 26.7 g of the titled compound (yield: 79%).

Reference Example 6

Synthesis of 2-methoxytriphenylamine

It can be synthesized by reacting according to the same manner as that described in Reference Example 1 except for using an equimolar amount of o-anisidine in place of 2,6-dimethylaniline.

Reference Example 7

Synthesis of 2-ethoxytriphenylamine

It can be synthesized by reacting according to the same manner as that described in Reference Example 1 except for using an equimolar amount of o-phenetidine in place of 2,6-dimethylaniline.

Reference Example 8

Synthesis of 2-methoxy-6-methyl-triphenylamine

It can be synthesized by reacting according to the same manner as that described in Reference Example 1 except for using an equimolar amount of 2-methoxy-6-methylaniline in place of 2,6-dimethylaniline.

Reference Example 9

Synthesis of 2-methoxy-5-methyl-triphenylamine

It can be synthesized by reacting according to the same manner as that described in Reference Example 1 except for using an equimolar amount of 2-methoxy-5-methylaniline in place of 2,6-dimethylaniline.

Reference Example 10

Synthesis of 5-methoxy-2-methyl-triphenylamine

It can be synthesized by reacting according to the same manner as that described in Reference Example 1 except for using an equimolar amount of 5-methoxy-2-methylaniline in place of 2,6-dimethylaniline.

Reference Example 11

Synthesis of 2,6-dimethyl-4'-formyltriphenylamine 2,6-dimethyltriphenylamine (28 g, 102 mmol) was dissolved in 300 ml of dimethylformamide (DMF) and phosphoric acid oxychloride (16 g, 104 mmol) was added, and the mixture was reacted at 40° C. for 1 hour. After the completion of the reaction, the reaction solution was added in 300 ml of water and extracted with ethyl acetate. The organic layer was washed with water and the solvent was distilled off by drying. Then, the residue was purified by silica gel chromatography (developing solvent: chloroform-hexane mixed solvent) to obtain 26.8 g of the titled compound (yield: 87%).

Reference Example 12

Synthesis of 2-ethyl-6-methyl-4'-formyltriphenylamine

According to the same manner as that described in Reference Example 11 except for using an equimolar amount of 2-ethyl-6-methyltriphenylamine in place of 2,6-dimethyltriphenylamine, the reaction was conducted to obtain 28.2 g of the titled compound (yield: 87%).

Reference Example 13

Synthesis of 2,6-diethyl-4'-formyltriphenylamine

According to the same manner as that described in Reference Example 11 except for using an equimolar amount of 2,6-diethyltriphenylamine in place of 2,6-dimethyltriphenylamine, the reaction was conducted to obtain 27.1 g of the titled compound (yield: 80%).

Reference Example 14

Synthesis of 2,3-dimethyl-4'-formyltriphenylamine

According to the same manner as that described in Reference Example 11 except for using an equimolar amount of 2,3-dimethyltriphenylamine in place of 2,6-dimethyltriphenylamine, the reaction was conducted to obtain 27.5 g of the titled compound (yield: 89%).

Reference Example 15

Synthesis of 2-ethyl-4'-formyltriphenylamine

According to the same manner as that described in Reference Example 11 except for using an equimolar amount of 2-ethyltriphenylamine in place of 2,6-dimethyltriphenylamine, the reaction was conducted to obtain 24.8 g of the titled compound (yield: 80%).

Reference Example 16

Synthesis of 2-methoxy-4'-formyltriphenylamine

It can be synthesized by reacting according to the same manner as that described in Reference Example 11 except for using an equimolar amount of 2-methoxytriphenylamine in place of 2,6-dimethyltriphenylamine.

Reference Example 17

Synthesis of 2-ethoxy-4'-formyltriphenylamine

It can be synthesized by reacting according to the same manner as that described in Reference Example 11 except for using an equimolar amount of 2-ethoxytriphenylamine in place of 2,6-dimethyltriphenylamine.

Reference Example 18

Synthesis of 2-methoxy-6-methyl-4'-formyltriphenylamine

It can be synthesized by reacting according to the same manner as that described in Reference Example 11 except for using an equimolar amount of 2-methoxy-6-methyltriphenylamine in place of 2,6-dimethyltriphenylamine.

Reference Example 19

Synthesis of 2-methoxy-5-methyl-4'-formyltriphenylamine

It can be synthesized by reacting according to the same manner as that described in Reference Example 11 except for using an equimolar amount of 2-methoxy-5-methyltriphenylamine in place of 2,6-dimethyltriphenylamine.

Reference Example 20

Synthesis of 5-methoxy-2-methyl-4'-formyltriphenylamine

It can be synthesized by reacting according to the same manner as that described in Reference Example 11 except for using an equimolar amount of 5-methoxy-2-methyltriphenylamine in place of 2,6-dimethyltriphenylamine.

Reference Example 21

Synthesis of Bisphosphate (3p)

In a flask equipped with Dean-Starn and a reflux condenser, 2,6-naphthalenedicarboxylic acid (10 g, 46 mmol), n-butanol (13.7 g, 185 mmol), 200 ml of toluene as a solvent and a catalytic amount of sulfuric acid were added and the mixture was refluxed for 8 hours. After the completion of the reaction, the reaction solution was concentrated and the resulting residue was recrystallized from methanol to obtain butyl 2,6-naphthalenedicarboxylate (12.8 g, 85%).

Then, a solution of lithium hydride (2.3 g, 60 mmol) in tetrahydrofuran (THF) was added in a flask equipped with a reflux condenser under an argon atmosphere. To the solution, a solution prepared by dissolving butyl 2,6-naphthalenedicarboxylate (10 g, 30 mmol) in 100 ml of tetrahydrofuran was slowly added dropwise and the mixture was reacted at room temperature for about 3 hours. After the completion of the reaction, the reaction solution was transferred in a ice bath and extracted with ethyl acetate. The resulting ethyl acetate layer was sufficiently washed with water and dried over anhydrous sodium sulfate, and then ethyl acetate was distilled off to obtain 2,6-naphthalenebishydroxymethyl (yield: 95%).

In the flask equipped with a reflux condenser, the resulting 2,6-naphthalenebishydroxymethyl (10 g, 53 mmol), 25 ml of thionyl chloride and pyridine (catalytic amount) as a phase transfer catalyst were added in order, and the mixture was refluxed for 8 hours. After the completion of the reaction, the solvent was distilled off and the resulting residue was recrystallized from methanol to obtain 2,6-naphthalenebischlorohydroxymethyl (yield: 80%).

In the flask equipped with a reflux condenser, the resulting 2,6-naphthalenebischlorohydroxymethyl (10 g, 44 mmol) and triethyl phosphate (17.7 g, 106 mmol) were added in order, and the mixture was refluxed for 4 hours. After the completion of the reaction, the solvent was distilled off and the resulting residue was recrystallized from hexane to obtain a bisphosphate derivative represented by the formula (3p) described below (yield: 80%).

Reference Example 22

Synthesis of Bisphosphate (3m)

According to the same manner as that described in Reference Example 21 except for using an equimolar amount of 1,4-naphthalenedicarboxylic acid in place of 2,6-naphthalenedicarboxylic acid, the reaction was conducted to obtain a bisphosphate derivative represented by the formula (3m) described below.

Reference Example 23

Synthesis of Bisphosphate (3n)

According to the same manner as that described in Reference Example 21 except for using an equimolar amount of 2,3-naphthalenedicarboxylic acid in place of 2,6-naphthalenedicarboxylic acid, the reaction was conducted to obtain a bisphosphate derivative represented by the formula (3n) described below.

The bisphosphate derivatives (3p) to (3n) obtained in Reference Examples 21 to 23 are as follows.

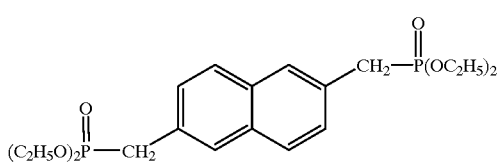

(3p)

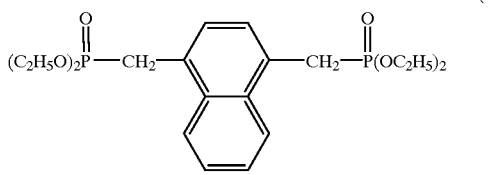

(3m)

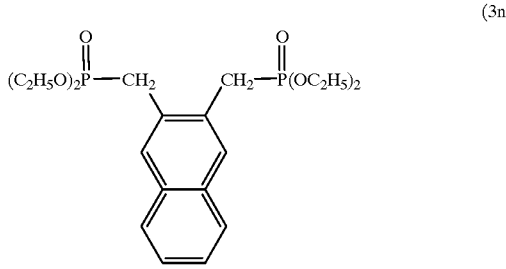

(3n)

Synthesis Example 1

Synthesis of Stilbene Derivative (11-2)

Bisphosphate represented by the formula (3p) (6.2 g, 15.6 mmol) and sodium hydride dried under deaeration (0.75 g, 31.2 mmol) were added in 200 ml of tetrahydrofuran, followed by ice-cooling. To this mixture, a solution prepared by dissolving 2,6-dimethyl-4'-formyltriphenylamine (9.5 g, 31.5 mmol) in 50 ml of tetrahydrofuran was added dropwise and the reaction was conducted at room temperature for about 3 hours. After the completion of the reaction, the reaction solution was added to 400 ml of an aqueous diluted hydrochloric acid solution (about 2%). The deposited crystal was collected by filtration, and then washed with water. The crystal was dried and purified by silica gel column chromatography (developing solvent: chloroform-hexane mixed solvent) to obtain 9.3 g of a stilbene derivative represented by the compound number 11-2 in Table 1 (yield: 83%).

Synthesis Example 2

Synthesis of Stilbene Derivative (11-6)

According to the same manner as that described in Synthesis Example 1 except for using an equimolar amount of 2-ethyl-6-methyl-4'-formyltriphenylamine in place of 2,6-dimethyl-4'-formyltriphenylamine, the reaction was conducted to obtain 10 g of a stilbene derivative represented by the compound number 11-6 in Table 1 (yield 85%).

Melting point: 244–246° C.

Figure 2:
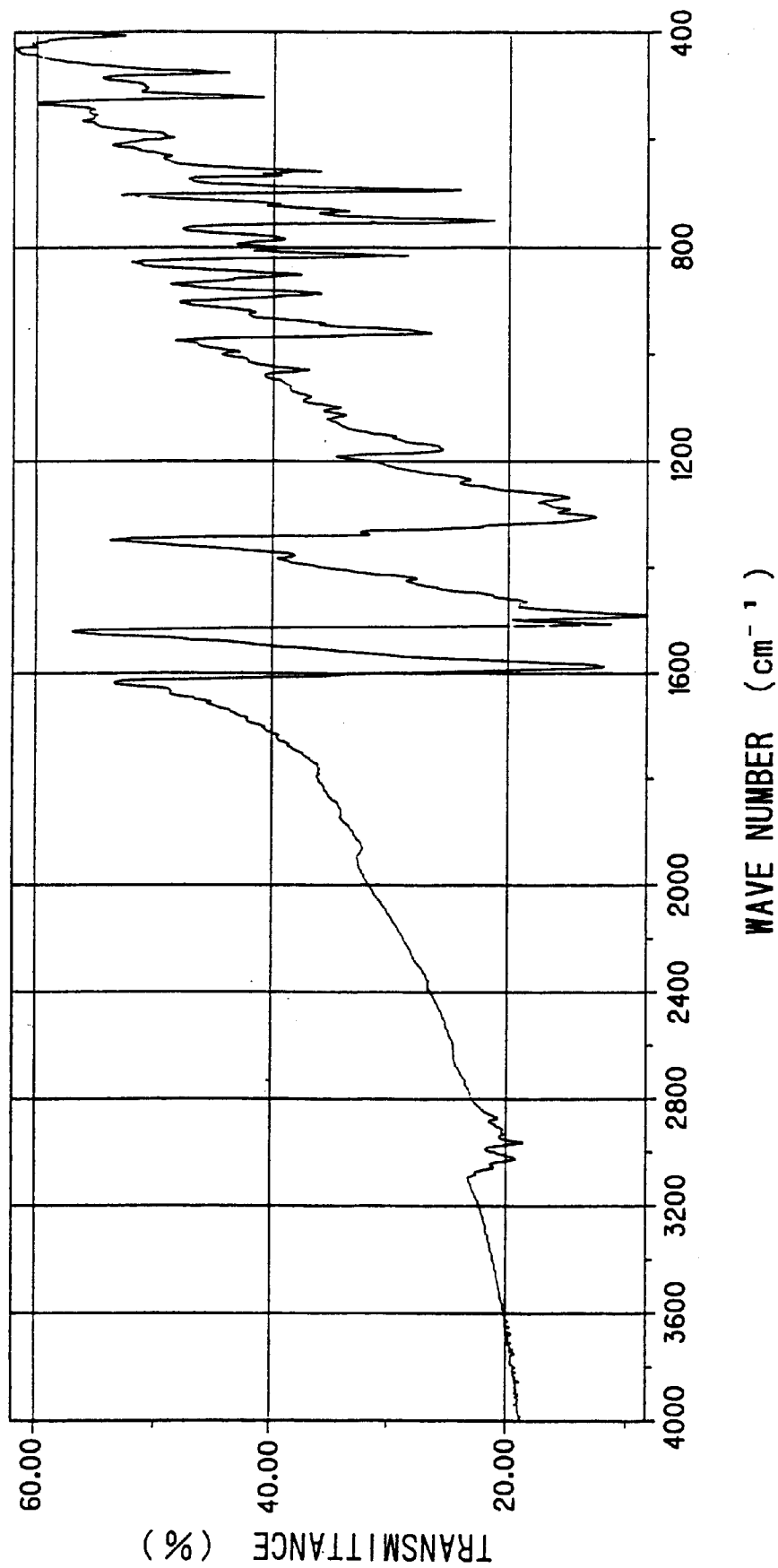
FIG. 2 is a graph showing an infrared absorption spectrum of the stilbene derivative (11-6).

The $^1$H-NMR spectrum of the stilbene derivative (11-6) is shown in FIG. 1 and the infrared absorption spectrum is shown in FIG. 2.

Synthesis Example 3

Synthesis of Stilbene Derivative (12-6)

According to the same manner as that described in Synthesis Example 1 except for using an equimolar amount of 2-ethyl-6-methyl-4'-formyltriphenylamine in place of 2,6-dimethyl-4'-formyltriphenylamine and using an equimolar amount of bisphosphate represented by the formula (3m) in place of bisphosphate represented by the formula (3p), the reaction was conducted to obtain 9.5 g of a stilbene derivative represented by the compound number 12-6 in Table 2 (yield 81%).

Synthesis Example 4

Synthesis of Stilbene Derivative (13-6)

According to the same manner as that described in Synthesis Example 1 except for using an equimolar amount of 2-ethyl-6-methyl-4'-formyltriphenylamine in place of 2,6-dimethyl-4'-formyltriphenylamine and using an equimolar amount of bisphosphate represented by the formula (3n) in place of bisphosphate represented by the formula (3p), the reaction was conducted to obtain 8.8 g of a stilbene derivative represented by the compound number 13-6 in Table 3 (yield 78%).

Synthesis Example 5

Synthesis of Stilbene Derivative (11-1)

According to the same manner as that described in Synthesis Example 1 except for using an equimolar amount of 2-methyl-4'-formyltriphenylamine in place of 2,6-dimethyl-4'-formyltriphenylamine, the reaction was conducted to obtain 9.0 g of a stilbene derivative represented by the compound number 11-1 in Table 1 (yield 80%).

Synthesis Example 6

Synthesis of Stilbene Derivative (11-7)

A stilbene derivative represented by the compound number 11-7 in Table 1 can be obtained by reacting according to the same manner as that described in Synthesis Example 1 except for using an equimolar amount of 2,6-diethyl-4'-formyltriphenylamine in place of 2,6-dimethyl-4'-formyltriphenylamine.

Synthesis Example 7

Synthesis of Stilbene Derivative (11-14)

A stilbene derivative represented by the compound number 11-14 in Table 1 can be obtained by reacting according to the same manner as that described in Synthesis Example 1 except for using an equimolar amount of 2-methoxy-4'-formyltriphenylamine in place of 2,6-dimethyl-4'-formyltriphenylamine.

Synthesis Example 8

Synthesis of Stilbene Derivative (11-15)

A stilbene derivative represented by the compound number 11-15 in Table 1 can be obtained by reacting according to to the same manner as that described in Synthesis Example 1 except for using an equimolar amount of 2-ethoxy-4'-formyltriphenylamine in place of 2,6-dimethyl-4'-formyltriphenylamine.

Synthesis Example 9

Synthesis of Stilbene Derivative (11-16)

A stilbene derivative represented by the compound number 11-16 in Table 1 can be obtained by reacting according to the same manner as that described in Synthesis Example 1 except for using an equimolar amount of 2-methoxy-6-methyl-4'-formyltriphenylamine in place of 2,6-diethyl-4'-formyltriphenylamine.

Synthesis Example 10

Synthesis of Stilbene Derivative (11-17)

A stilbene derivative represented by the compound number 11-17 in Table 1 can be obtained by reacting according to the same manner as that described in Synthesis Example 1 except for using an equimolar amount of 2-methoxy-5-methyl-4'-formyltriphenylamine in place of 2,6-dimethyl-4'-formyltriphenylamine.

Synthesis Example 11

Synthesis of Stilbene Derivative (11-18)

A stilbene derivative represented by the compound number 11-18 in Table 1 can be obtained by reacting according to the same manner as that described in Synthesis Example 1 except for using an equimolar amount of 5-methoxy-2-methyl-4'-formyltriphenylamine in place of 2,6-dimethyl-4'-formyltriphenylamine.

Synthesis Example 12

Synthesis of Stilbene Derivative (12-2)

A stilbene derivative represented by the compound number 12-2 in Table 2 can be obtained by reacting according to the same manner as that described in Synthesis Example 1 except for using an equimolar amount of bisphosphate represented by the formula (3m) in place of bisphosphate represented by the formula (3p).

Synthesis Example 13

Synthesis of Stilbene Derivative (12-1)

A stilbene derivative represented by the compound number 12-1 in Table 2 can be obtained by reacting according to the same manner as that described in Synthesis Example 1 except for using an equimolar amount of 2-methyl-4'-formyltriphenylamine in place of 2,6-dimethyl-4'-formyltriphenylamine and using an equimolar amount of bisphosphate represented by the formula (3m) in place of bisphosphate represented by the formula (3p).

Synthesis Example 14

Synthesis of Stilbene Derivative (12-7)

A stilbene derivative represented by the compound number 12-7 in Table 2 can be obtained by reacting according to the same manner as that described in Synthesis Example 1 except for using an equimolar amount of 2,6-diethyl-4'-formyltriphenylamine in place of 2,6-dimethyl-4'-formyltriphenylamine and using an equimolar amount of bisphosphate represented by the formula (3m) in place of bisphosphate represented by the formula (3p).

Synthesis Example 15

Synthesis of Stilbene Derivative (12-14)

A stilbene derivative represented by the compound number 12-14 in Table 2 can be obtained by reacting according to the same manner as that described in Synthesis Example 1 except for using an equimolar amount of 2-methoxy-4'-formyltriphenylamine in place of 2,6-dimethyl-4'-formyltriphenylamine and using an equimolar amount of bisphosphate represented by the formula (3m) in place of bisphosphate represented by the formula (3p).

Synthesis Example 16

Synthesis of Stilbene Derivative (12-15)

A stilbene derivative represented by the compound number 12-15 in Table 2 can be obtained by reacting according to the same manner as that described in Synthesis Example 1 except for using an equimolar amount of 2-ethoxy-4'-formyltriphenylamine in place of 2,6-dimethyl-4'-formyltriphenylamine and using an equimolar amount of bisphosphate represented by the formula (3m) in place of bisphosphate represented by the formula (3p).

Synthesis Example 17

Synthesis of Stilbene Derivative (12-16)

A stilbene derivative represented by the compound number 12-16 in Table 2 can be obtained by reacting according to the same manner as that described in Synthesis Example 1 except for using an equimolar amount of 2-methoxy-6-methyl-4'-formyltriphenylamine in place of 2,6-dimethyl-4'-formyltriphenylamine and using an equimolar amount of bisphosphate represented by the formula (3m) in place of bisphosphate represented by the formula (3p).

Synthesis Example 18

Synthesis of Stilbene Derivative (12-17)

A stilbene derivative represented by the compound number 12-17 in Table 2 can be obtained by reacting according to the same manner as that described in Synthesis Example 1 except for using an equimolar amount of 2-methoxy-5-methyl-4'-formyltriphenylamine in place of 2,6-dimethyl-4'-formyltriphenylamine and using an equimolar amount of bisphosphate represented by the formula (3m) in place of bisphosphate represented by the formula (3p).

Synthesis Example 19

Synthesis of Stilbene Derivative (12-18)

A stilbene derivative represented by the compound number 12-18 in Table 2 can be obtained by reacting according to the same manner as that described in Synthesis Example 1 except for using an equimolar amount of 5-methoxy-2-methyl-4'-formyltriphenylamine in place of 2,6-dimethyl-4'-formyltriphenylamine and using an equimolar amount of bisphosphate represented by the formula (3m) in place of bisphosphate represented by the formula (3p).

Synthesis Example 20

Synthesis of Stilbene Derivative (13-2)

A stilbene derivative represented by the compound number 13-2 in Table 3 can be obtained by reacting according to

Synthesis Example 21

Synthesis of Stilbene Derivative (13-1)

A stilbene derivative represented by the compound number 13-1 in Table 3 can be obtained by reacting according to the same manner as that described in Synthesis Example 1 except for using an equimolar amount of 2-methyl-4'-formyltriphenylamine in place of 2,6-dimethyl-4'-formyltriphenylamine and using an equimolar amount of bisphosphate represented by the formula (3n) in place of bisphosphate represented by the formula (3p).

Synthesis Example 22

Synthesis of Stilbene Derivative (13-7)

A stilbene derivative represented by the compound number 13-7 in Table 3 can be obtained by reacting according to the same manner as that described in Synthesis Example 1 except for using an equimolar amount of 2,6-diethyl-4'-formyltriphenylamine in place of 2,6-dimethyl-4'-formyltriphenylamine and using an equimolar amount of bisphosphate represented by the formula (3n) in place of bisphosphate represented by the formula (3p).

Synthesis Example 23

Synthesis of Stilbene Derivative (13-14)

A stilbene derivative represented by the compound number 13-14 in Table 3 can be obtained by reacting according to the same manner as that described in Synthesis Example 1 except for using an equimolar amount of 2-methyl-4'-formyltriphenylamine in place of 2-methoxy-4'-formyltriphenylamine and using an equimolar amount of bisphosphate represented by the formula (3n) in place of bisphosphate represented by the formula (3p).

Synthesis Example 24

Synthesis of Stilbene Derivative (13-15)

A stilbene derivative represented by the compound number 13-15 in Table 3 can be obtained by reacting according to the same manner as that described in Synthesis Example 1 except for using an equimolar amount of 2-ethoxy-4'-formyltriphenylamine in place of 2,6-dimethyl-4'-formyltriphenylamine and using an equimolar amount of bisphosphate represented by the formula (3n) in place of bisphosphate represented by the formula (3p).

Synthesis Example 25

Synthesis of Stilbene Derivative (13-16)

A stilbene derivative represented by the compound number 13-16 in Table 3 can be obtained by reacting according to the same manner as that described in Synthesis Example 1 except for using an equimolar amount of 2-methoxy-6-methyl-4'-formyltriphenylamine in place of 2,6-dimethyl-4'-formyltriphenylamine and using an equimolar amount of bisphosphate represented by the formula (3n) in place of bisphosphate represented by the formula (3p).

Synthesis Example 26

Synthesis of Stilbene Derivative (13-17)

A stilbene derivative represented by the compound number 13-17 in Table 3 can be obtained by reacting according to the same manner as that described in Synthesis Example 1 except for using an equimolar amount of 2-methoxy-5-methyl-4'-formyltriphenylamine in place of 2,6-dimethyl-4'-formyltriphenylamine and using an equimolar amount of bisphosphate represented by the formula (3n) in place of bisphosphate represented by the formula (3p).

Synthesis Example 27

Synthesis of Stilbene Derivative (13-18)

A stilbene derivative represented by the compound number 13-18 in Table 3 can be obtained by reacting according to the same manner as that described in Synthesis Example 1 except for using an equimolar amount of 5-methoxy-2-methyl-4'-formyltriphenylamine in place of 2,6-dimethyl-4'-formyltriphenylamine and using an equimolar amount of bisphosphate represented by the formula (3n) in place of bisphosphate represented by the formula (3p).

Evaluation of Compatibility With Binding Resin

Test Example 1

With respect to each of the stilbene derivatives obtained in Synthesis Examples 1 to 5, the compatibility with a binding resin was evaluated by the following procedure.

Preparation of Sample

A mixed solution of 100 parts by weight of a binding resin (polycarbonate) and 800 parts by weight of a solvent (tetrahydrofuran) was mixed with each of 1 to 100 parts by weight of the stilbene derivatives obtained in Synthesis Examples 1 to 5, and then a maximum amount (parts by weight) enough to give a uniform coating solution of the stilbene derivative was determined. The coating solution was prepared by mixing and dispersing the above components in a ball mill for 50 hours.

Then, a mixing ratio (% by weight) of the stilbene derivative to the binding resin was determined by substituting the maximum amount (parts by weight) of the above each stilbene derivative into the following equation and the compatibility with the binding resin was evaluated. The higher this mixing ratio, the higher the solubility in the binding resin, resulting in excellent compatibility with the binding resin.

Mixing ratio (% by weight)=amount of stilbene derivative×100/amount of binding resin With respect to the stilbene derivatives represented by the following formulas (6-1) to (6-7) as a control compound, the solubility in the binding resin was evaluated in the same manner as described above.

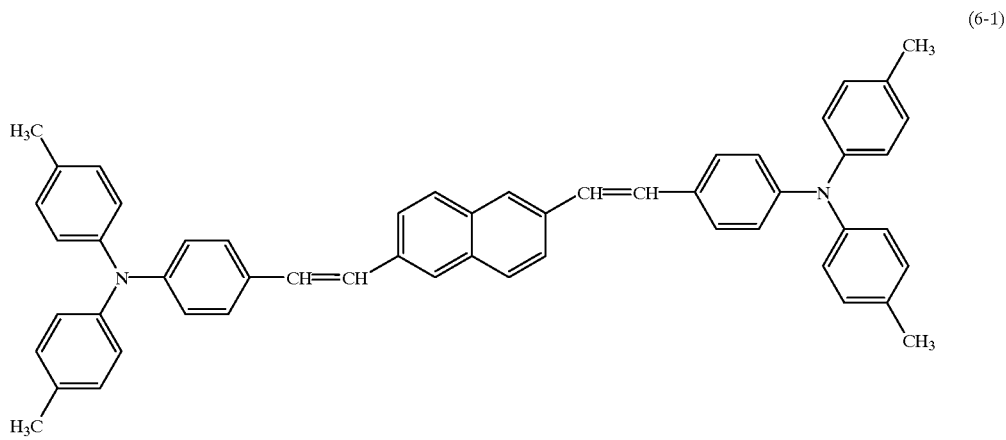
(6-1)
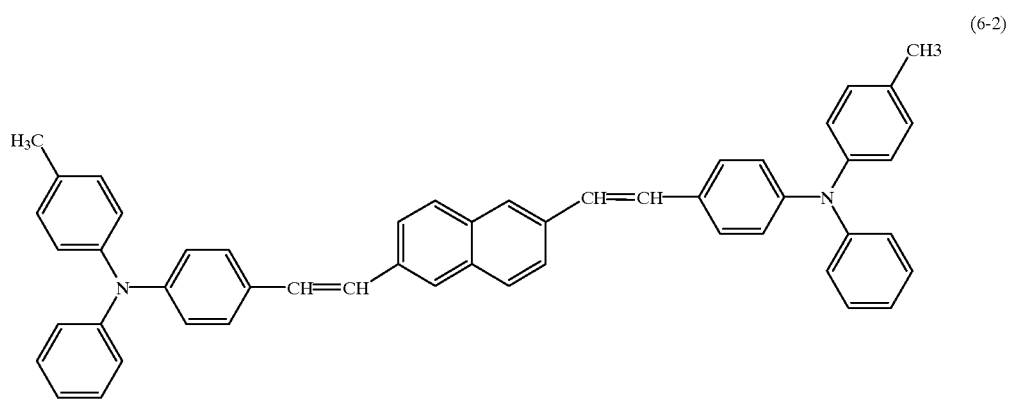
(6-2)
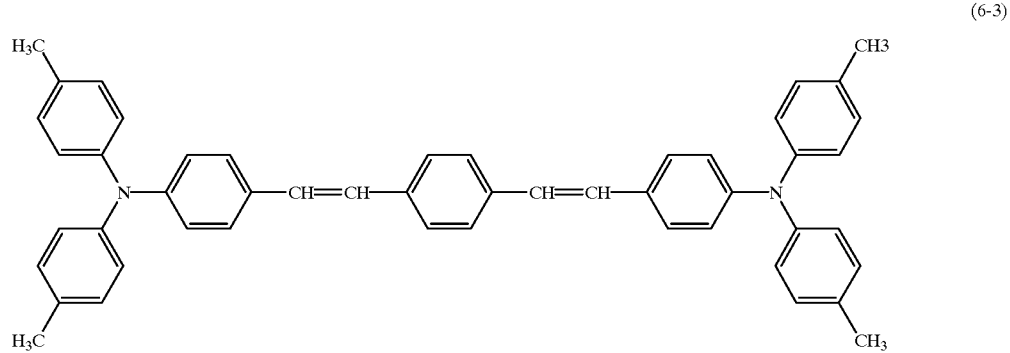
(6-3)
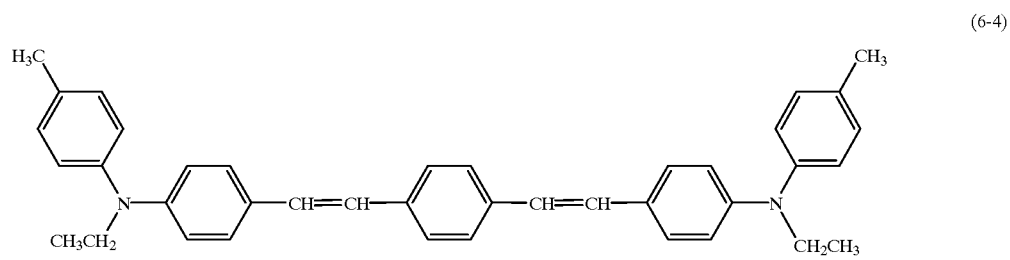
(6-4)

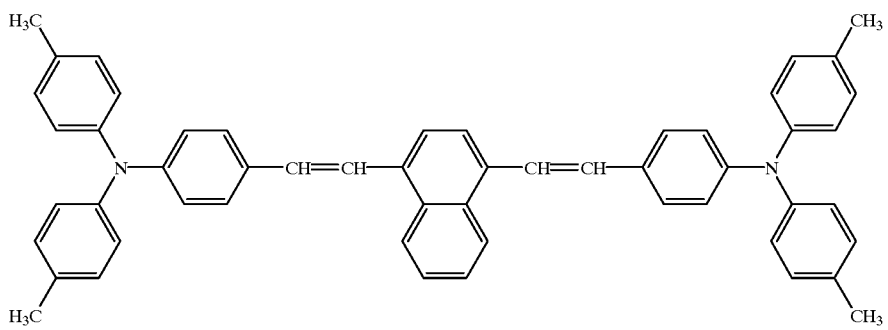

(6-5)

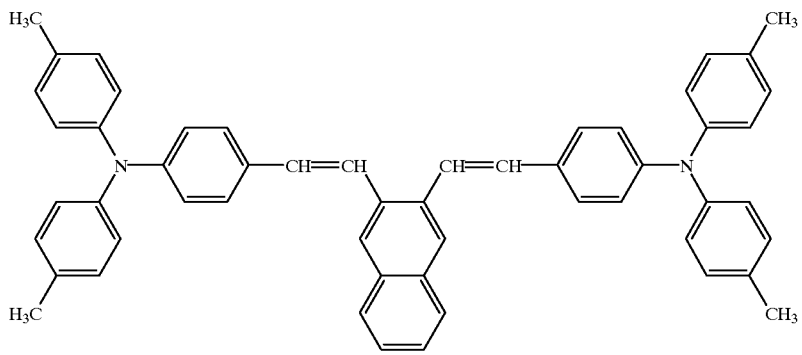

(6-6)

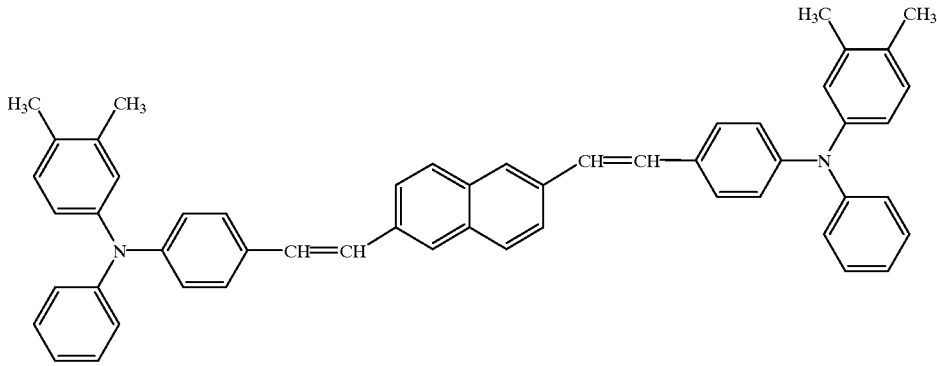

(6-7)

These results are shown in Table 4 below.

TABLE 4

| Compound number | Compatibility with binding resin (% by weight) |
| --- | --- |
| 11-1 | 100 or more |
| 11-2 | 100 or more |
| 11-6 | 100 or more |
| 12-6 | 100 or more |
| 13-6 | 100 or more |
| 6-1 | 13 |
| 6-2 | 12 |
| 6-3 | 11 |
| 6-4 | 12 |
| 6-5 | 12 |
| 6-6 | 16 |
| 6-7 | 15 |

As is apparent from Table 4, the stilbene derivatives obtained in Synthesis Examples 1 to 5 are remarkably superior in solubility in the binding resin to the stilbene derivatives (6-1) to (6-7) as the control compound.

Production of Electrophotosemsitive Material

Single-Layer Type Photosensitive Material for Digital Light Source

Example 1

A X type melt-free phthalocyanine (CG1-1) was used as the electric charge generating material. A stilbene derivative represented by the compound number (11-2) in Table 1 was used as the hole transferring material.

5 Parts by weight of the above electric charge generating material, 100 parts by weight of the above hole transferring material and 100 parts by weight of a binding resin (polycarbonate) were mixed and dispersed, together with 800 parts by weight of a solvent (tetrahydrofuran), in a ball mill for 50 hours to prepare a coating solution for single-layer type photosensitive layer. Then, this coating solution was applied on a conductive substrate (alumina tube) by using the dip coating method, followed by hot-air drying at 100° C. for 30 minutes to obtain a single-layer type photosensitive material for digital light source, which has a single-layer type photosensitive layer of 25 μm in film thickness.

Example 2

According to the same manner as that described in Example 1 except for using a stilbene derivative represented by the compound number (11-6) in Table 1 as the hole transferring material, a single-layer type photosensitive material for digital light source was produced.

Example 3

According to the same manner as that described in Example 1 except for using a stilbene derivative represented by the compound number (12-6) in Table 2 as the hole transferring material, a single-layer type photosensitive material for digital light source was produced.

Example 4

According to the same manner as that described in Example 1 except for using a stilbene derivative represented by the compound number (13-6) in Table 3 as the hole transferring material, a single-layer type photosensitive material for digital light source was produced.

Example 5

According to the same manner as that described in Example 1 except for further mixing 30 parts by weight of a diphenoquinone derivative represented by the formula (ET17-1):

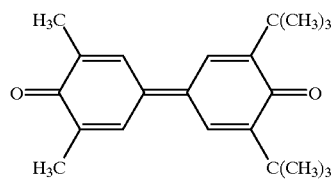

(ET17-1)

with the coating solution for single-layer type photosensitive layer, a single-layer type photosensitive material for digital light source was produced.

Example 6

According to the same manner as that described in Example 5 except for using a stilbene derivative represented by the compound number (11-6) as the hole transferring material, a single-layer type photosensitive material for digital light source was produced.

Example 7

According to the same manner as that described in Example 5 except for using a stilbene derivative represented by the compound number (12-6) as the hole transferring material, a single-layer type photosensitive material for digital light source was produced.

Example 8

According to the same manner as that described in Example 5 except for using a stilbene derivative represented by the compound number (13-6) as the hole transferring material, a single-layer type photosensitive material for digital light source was produced.

Examples 9 to 12

According to the same manner as that described in Examples 5 to 8 except for using a compound represented by the formula (ET14-1):

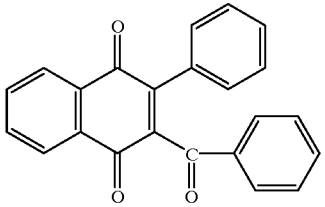

(ET14-1)

as the electron transferring material, single-layer type photosensitive materials for digital light source were produced, respectively.

Examples 13 to 16

According to the same manner as that described in Examples 5 to 8 except for using a compound represented by the formula (ET14-2):

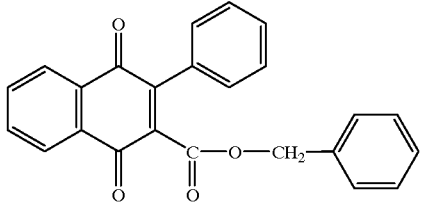

(ET14-2)

as the electron transferring material, single-layer type photosensitive materials for digital light source were produced, respectively.

Comparative Example 1

According to the same manner as that described in Example 1 except for using a stilbene derivative represented by the formula (6-1):

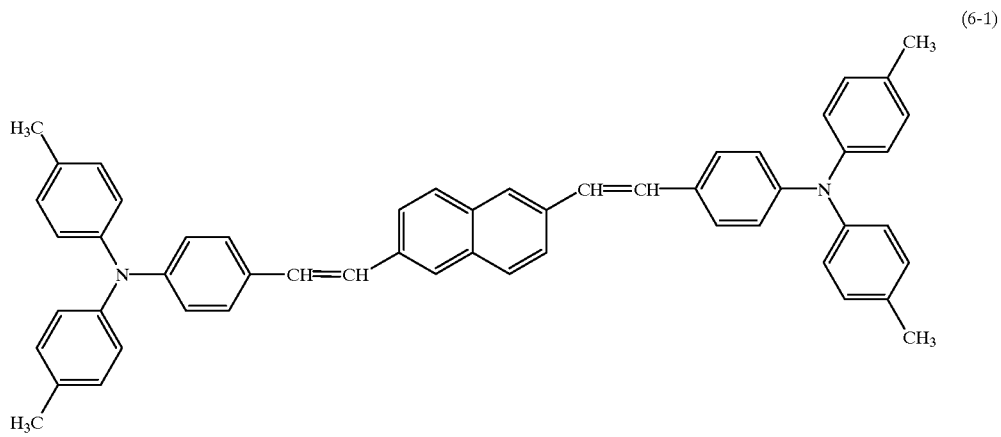

(6-1)

as the hole transferring material, a single-layer type photosensitive materials for digital light source was produced.

Comparative Example 2

According to the same manner as that described in Example 1 except for using a stilbene derivative represented by the formula (6-2):

as the hole transferring material, a single-layer type photosensitive materials for digital light source was produced.

Comparative Example 3

According to the same manner as that described in Example 1 except for using a stilbene derivative represented by the formula (6-3):

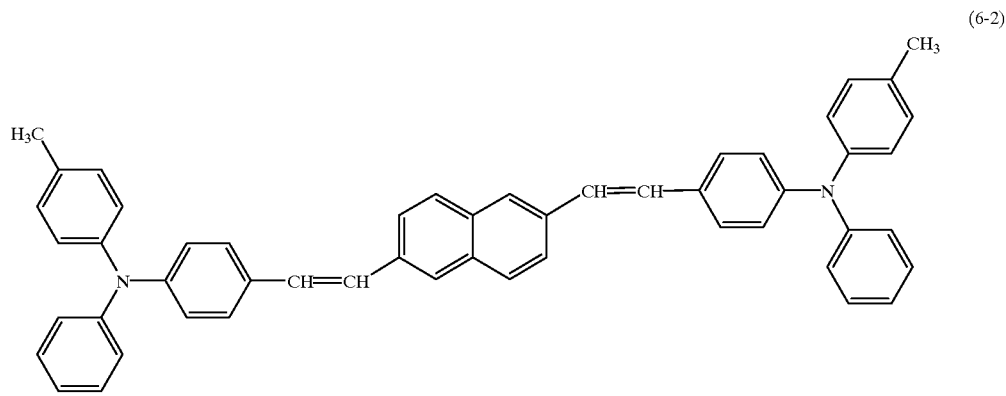

(6-2)

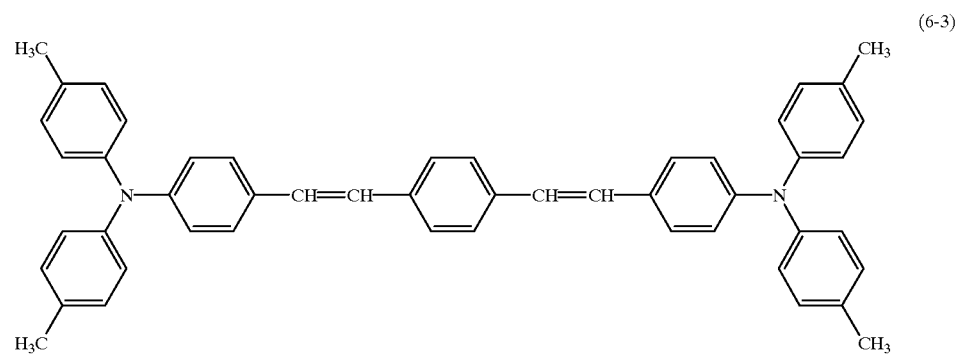

(6-3)

as the hole transferring material, a single-layer type photosensitive materials for digital light source was produced.

Comparative Example 4

According to the same manner as that described in Example 1 except for using a stilbene derivative represented by the formula (6-4):

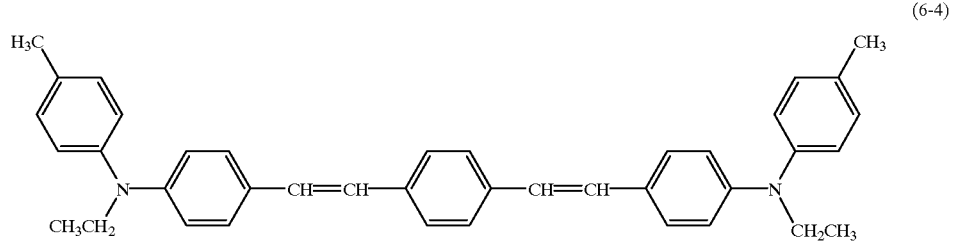

(6-4)

as the hole transferring material, a single-layer type photosensitive materials for digital light source was produced.

Comparative Example 5

According to the same manner as that described in Example 1 except for using a stilbene derivative represented by the formula (6-5):

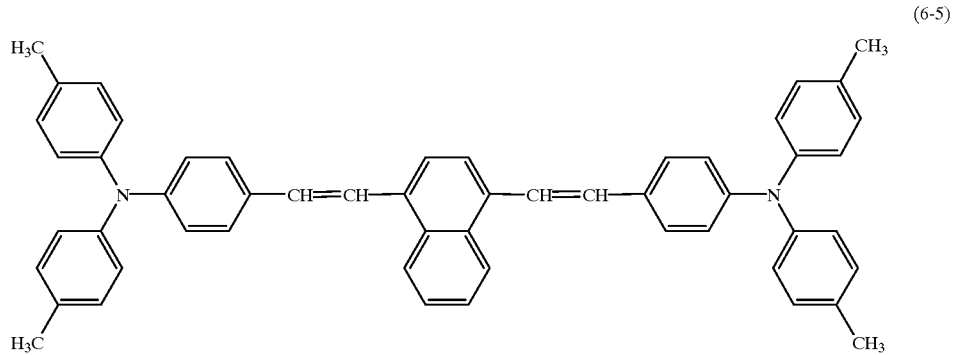

(6-5)

as the hole transferring material, a single-layer type photosensitive materials for digital light source was produced.

Comparative Example 6

According to the same manner as that described in Example 1 except for using a stilbene derivative represented by the formula (6-6):

(6-6)

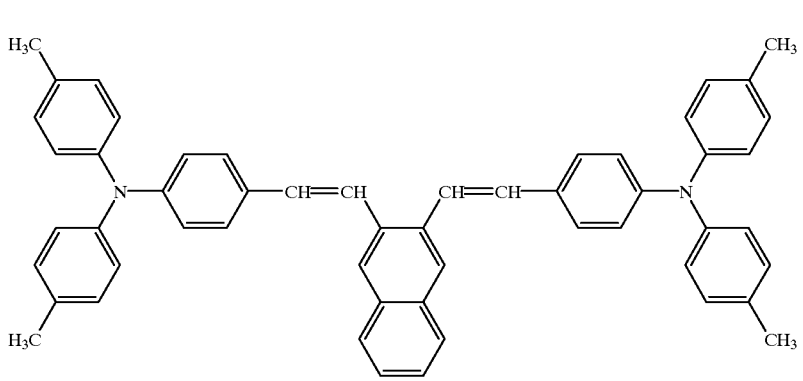

as the hole transferring material, a single-layer type photosensitive materials for digital light source was produced.

Comparative Example 7

According to the same manner as that described in Example 1 except for using a stilbene derivative represented by the formula (6-7):

(6-7)

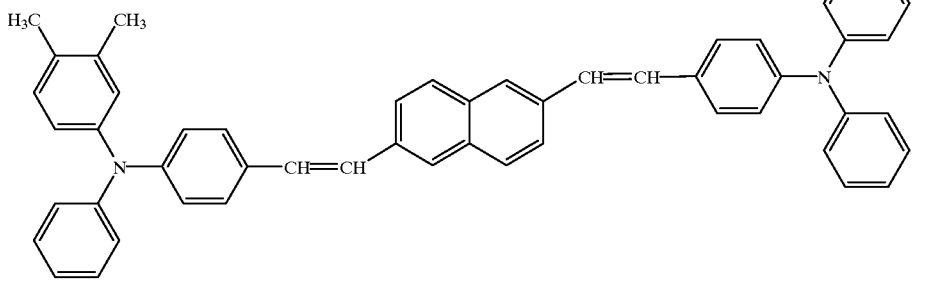

as the hole transferring material, a single-layer type photosensitive materials for digital light source was produced.

The photosensitive materials obtained in Examples 1 to 16 and Comparative Examples 1 to 7 were subjected to the following electrical characteristics test (I) and the electrical characteristics of the respective photosensitive materials were evaluated, respectively.

Electrical Characteristics Test (I)

Using a drum sensitivity tester manufactured by GENETEC Co., a voltage was applied on the surface of each photosensitive material to charge the surface at +700 V±20 V and the surface potential $V_o$ (V) was measured. Then, monochromic light having a wavelength of 780 nm (half-width: 20 nm, light intensity: 8 $\mu W/cm^2$) from white light of a halogen lamp as an exposure light source through a band-pass filter was irradiated on the surface of each photosensitive material (irradiation time: 1.5 seconds) and the time required to reduce the above surface potential $V_o$ to half was measured and a half-life exposure $E_{1/2}$ ($\mu J/cm^2$) was calculated. Furthermore, a surface potential at the time at which 0.5 seconds have passed since the beginning of exposure was measured as a residual potential $V_r$ (V).

The kind of the electric charge generating material, hole transferring material and electron transferring material used in the above respective Examples and Comparative Examples as well as test results of the electrical characteristics are shown in Table 5. In the following tables, the electric charge generating material, hole transferring material and electron transferring material were represented by each formula number or each compound number.

TABLE 5

|  | Electric charge generating material | Hole transferring material | Electron transferring material | $V_o$ | $V_r$ | $E_{1/2}$ |
| --- | --- | --- | --- | --- | --- | --- |
| Example 1 | CG1-1 | 11-2 | — | 700 | 118 | 0.73 |
| Example 2 | CG1-1 | 11-6 | — | 702 | 115 | 0.74 |
| Example 3 | CG1-1 | 12-6 | — | 699 | 116 | 0.74 |
| Example 4 | CG1-1 | 13-6 | — | 700 | 130 | 0.79 |
| Example 5 | CG1-1 | 11-2 | ET17-1 | 703 | 96 | 0.69 |
| Example 6 | CG1-1 | 11-6 | ET17-1 | 702 | 95 | 0.68 |
| Example 7 | CG1-1 | 12-6 | ET17-1 | 701 | 97 | 0.67 |
| Example 8 | CG1-1 | 13-6 | ET17-1 | 699 | 102 | 0.77 |
| Example 9 | CG1-1 | 11-2 | ET14-1 | 703 | 99 | 0.70 |
| Example 10 | CG1-1 | 11-6 | ET14-1 | 702 | 100 | 0.69 |
| Example 11 | CG1-1 | 12-6 | ET14-1 | 701 | 101 | 0.69 |
| Example 12 | CG1-1 | 13-6 | ET14-1 | 704 | 113 | 0.76 |

TABLE 5-continued

| | Electric charge generating material | Hole transferring material | Electron transferring material | $V_o$ | $V_r$ | $E_{1/2}$ |
|---|---|---|---|---|---|---|
| Example 13 | CG1-1 | 11-2 | ET14-2 | 701 | 92 | 0.68 |
| Example 14 | CG1-1 | 11-6 | ET14-2 | 702 | 91 | 0.67 |
| Example 15 | CG1-1 | 12-6 | ET14-2 | 703 | 93 | 0.66 |
| Example 16 | CG1-1 | 13-6 | ET14-2 | 700 | 102 | 0.75 |
| Comp. Example 1 | CG1-1 | 6-1 | — | 699 | 144 | 0.80 |
| Comp. Example 2 | CG1-1 | 6-2 | — | 700 | 146 | 0.82 |
| Comp. Example 3 | CG1-1 | 6-3 | — | 701 | 152 | 0.85 |
| Comp. Example 4 | CG1-1 | 6-4 | — | 703 | 158 | 0.91 |
| Comp. Example 5 | CG1-1 | 6-5 | — | 702 | 143 | 0.80 |
| Comp. Example 6 | CG1-1 | 6-6 | — | 691 | 151 | 0.90 |
| Comp. Example 7 | CG1-1 | 6-7 | — | 702 | 144 | 0.81 |

Examples 17 to 20

According to the same manner as that described in Examples 1 to 4 except for using an α type oxotitanylphthalocyanine (CG2-1) as the electric charge generating material, single-layer type photosensitive materials for digital light source were produced, respectively.

Examples 21 to 24

According to the same manner as that described in Examples 5 to 8 except for using an α type oxotitanylphthalocyanine (CG2-1) as the electric charge generating material, single-layer type photosensitive materials for digital light source were produced, respectively.

Examples 25 to 28

According to the same manner as that described in Examples 9 to 12 except for using an α type oxotitanylphthalocyanine (CG2-1) as the electric charge generating material, single-layer type photosensitive materials for digital light source were produced, respectively.

Examples 29 to 32

According to the same manner as that described in Examples 13 to 16 except for using an α type oxotitanylphthalocyanine (CG2-1) as the electric charge generating material, single-layer type photosensitive materials for digital light source were produced, respectively.

Comparative Examples 8 to 14

According to the same manner as that described in Comparative Examples 1 to 7 except for using an α type oxotitanylphthalocyanine (CG2-1) as the electric charge generating material, single-layer type photosensitive materials for digital light source were produced, respectively.

The photosensitive materials obtained in Examples 17 to 32 and Comparative Examples 8 to 14 were subjected to the following electrical characteristics test (I) and the electrical characteristics of the respective photosensitive materials were evaluated, respectively. The kind of the electric charge generating material, hole transferring material and electron transferring material used in the above respective Examples and Comparative Examples as well as test results of the electrical characteristics are shown in Table 6.

TABLE 6

| | Electric charge generating material | Hole transferring material | Electron transferring material | $V_o$ | $V_r$ | $E_{1/2}$ |
|---|---|---|---|---|---|---|
| Example 17 | CG2-1 | 11-2 | — | 701 | 117 | 0.73 |
| Example 18 | CG2-1 | 11-6 | — | 702 | 116 | 0.73 |
| Example 19 | CG2-1 | 12-6 | — | 700 | 117 | 0.74 |
| Example 20 | CG2-1 | 13-6 | — | 699 | 121 | 0.80 |
| Example 21 | CG2-1 | 11-2 | ET17-1 | 698 | 95 | 0.70 |
| Example 22 | CG2-1 | 11-6 | ET17-1 | 702 | 94 | 0.71 |
| Example 23 | CG2-1 | 12-6 | ET17-1 | 701 | 95 | 0.72 |
| Example 24 | CG2-1 | 13-6 | ET17-1 | 704 | 103 | 0.81 |
| Example 25 | CG2-1 | 11-2 | ET14-1 | 702 | 100 | 0.71 |
| Example 26 | CG2-1 | 11-6 | ET14-1 | 701 | 100 | 0.70 |
| Example 27 | CG2-1 | 12-6 | ET14-1 | 703 | 99 | 0.71 |
| Example 28 | CG2-1 | 13-6 | ET14-1 | 702 | 111 | 0.89 |
| Example 29 | CG2-1 | 11-2 | ET14-2 | 699 | 92 | 0.69 |
| Example 30 | CG2-1 | 11-6 | ET14-2 | 700 | 91 | 0.68 |
| Example 31 | CG2-1 | 12-6 | ET14-2 | 701 | 90 | 0.67 |
| Example 32 | CG2-1 | 13-6 | ET14-2 | 702 | 101 | 0.78 |
| Comp. Example 8 | CG2-1 | 6-1 | — | 701 | 136 | 0.80 |
| Comp. Example 9 | CG2-1 | 6-2 | — | 702 | 139 | 0.81 |
| Comp. Example 10 | CG2-1 | 6-3 | — | 703 | 141 | 0.83 |
| Comp. Example 11 | CG2-1 | 6-4 | — | 701 | 147 | 0.84 |
| Comp. Example 12 | CG2-1 | 6-5 | — | 699 | 138 | 0.81 |
| Comp. Example 13 | CG2-1 | 6-6 | — | 706 | 149 | 0.84 |
| Comp. Example 14 | CG2-1 | 6-7 | — | 703 | 138 | 0.81 |

Examples 33 to 36

According to the same manner as that described in Examples 1 to 4 except for using a Y type oxotitanylphthalocyanine (CG2-2) as the electric charge generating material, single-layer type photosensitive materials for digital light source were produced, respectively.

Examples 37 to 40

According to the same manner as that described in Examples 5 to 8 except for using a Y type oxotitanylphthalocyanine (CG2-2) as the electric charge generating material, single-layer type photosensitive materials for digital light source were produced, respectively.

Examples 41 to 44

According to the same manner as that described in Examples 9 to 12 except for using a Y type oxotitanylphthalocyanine (CG2-2) as the electric charge generating material, single-layer type photosensitive materials for digital light source were produced, respectively.

Examples 45 to 48

According to the same manner as that described in Examples 13 to 16 except for using a Y type oxotitanylphthalocyanine (CG2-2) as the electric charge generating material, single-layer type photosensitive materials for digital light source were produced, respectively.

Comparative Examples 15 to 21

According to the same manner as that described in Comparative Examples 1 to 7 except for using a Y type oxotitanylphthalocyanine (CG2-2) as the electric charge generating material, single-layer type photosensitive materials for digital light source were produced, respectively.

The photosensitive materials obtained in Examples 33 to 48 and Comparative Examples 15 to 21 were subjected to the following electrical characteristics test (I) and the electrical characteristics of the respective photosensitive materials were evaluated, respectively. The kind of the electric charge generating material, hole transferring material and electron transferring material used in the above respective Examples and Comparative Examples as well as test results of the electrical characteristics are shown in Table 7.

TABLE 7

|  | Electric charge generating material | Hole trans- ferring material | Electron trans- ferring material | $V_o$ | $V_r$ | $E_{1/2}$ |
|---|---|---|---|---|---|---|
| Example 33 | CG2-2 | 11-2 | — | 703 | 118 | 0.67 |
| Example 34 | CG2-2 | 11-6 | — | 702 | 118 | 0.66 |
| Example 35 | CG2-2 | 12-6 | — | 700 | 116 | 0.68 |
| Example 36 | CG2-2 | 13-6 | — | 698 | 127 | 0.75 |
| Example 37 | CG2-2 | 11-2 | ET17-1 | 698 | 95 | 0.64 |
| Example 38 | CG2-2 | 11-6 | ET17-1 | 697 | 94 | 0.64 |
| Example 39 | CG2-2 | 12-6 | ET17-1 | 700 | 95 | 0.65 |
| Example 40 | CG2-2 | 13-6 | ET17-1 | 701 | 105 | 0.71 |
| Example 41 | CG2-2 | 11-2 | ET14-1 | 704 | 99 | 0.62 |
| Example 42 | CG2-2 | 11-6 | ET14-1 | 702 | 98 | 0.63 |
| Example 43 | CG2-2 | 12-6 | ET14-1 | 701 | 97 | 0.62 |
| Example 44 | CG2-2 | 13-6 | ET14-1 | 703 | 115 | 0.72 |
| Example 45 | CG2-2 | 11-2 | ET14-2 | 702 | 91 | 0.63 |
| Example 46 | CG2-2 | 11-6 | ET14-2 | 701 | 90 | 0.64 |
| Example 47 | CG2-2 | 12-6 | ET14-2 | 700 | 90 | 0.63 |
| Example 48 | CG2-2 | 13-6 | ET14-2 | 699 | 101 | 0.72 |
| Comp. Example 15 | CG2-2 | 6-1 | — | 701 | 132 | 0.79 |
| Comp. Example 16 | CG2-2 | 6-2 | — | 703 | 133 | 0.81 |
| Comp. Example 17 | CG2-2 | 6-3 | — | 702 | 141 | 0.85 |
| Comp. Example 18 | CG2-2 | 6-4 | — | 701 | 148 | 0.87 |
| Comp. Example 19 | CG2-2 | 6-5 | — | 702 | 134 | 0.81 |
| Comp. Example 20 | CG2-2 | 6-6 | — | 701 | 144 | 0.85 |
| Comp. Example 21 | CG2-2 | 6-7 | — | 700 | 135 | 0.81 |

Multi-Layer Type Photosensitive Material for Digital Light Source

Example 49

2.5 Parts by weight of a X type metal-free phthalocyanine (CG1-1) as the electric charge generating material and 1 part by weight of a binding resin (polyvinyl butyral) were mixed and dispersed, together with 15 parts by weight of a solvent (tetrahydrofuran), in a ball mill to prepare a coating solution for electric charge generating layer. Then, this coating solution was applied on a conductive substrate (aluminum tube) by using the dip coating method, followed by hot-air drying at 110 for 30 minutes to form an electric charge generating layer of 0.5 $\mu$m in film thickness.

Then, 1 part by weight of a stilbene derivative (11-2) as the hole transferring material and 1 part of a binding resin (polycarbonate) were mixed and dispersed, together with 10 parts by weight of a solvent (tetrahydrofuran), in a ball mill to prepare a coating solution for electric charge transferring layer. Then, this coating solution was applied on the above electric charge generating layer by using the dip coating method, followed by hot-air drying at 110 for 30 minutes to form an electric charge transferring layer of 20 $\mu$m in film thickness, thereby producing a multi-layer type photosensitive material.

Example 50

According to the same manner as that described in Example 49 except for using a stilbene derivative (11-6) as the hole transferring material, a multi-layer type photosensitive material for digital light source was produced.

Example 51

According to the same manner as that described in Example 49 except for using a stilbene derivative (12-6) as the hole transferring material, a multi-layer type photosensitive material for digital light source was produced.

Example 52

According to the same manner as that described in Example 49 except for using a stilbene derivative (13-6) as the hole transferring material, a multi-layer type photosensitive material for digital light source was produced.

Examples 53 to 56

According to the same manner as that described in Examples 49 to 52 except for using an α type oxotitanylphthalocyanine (CG2-1) as the electric charge generating material, a multi-layer type photosensitive material for digital light source were produced, respectively.

Examples 57 to 60

According to the same manner as that described in Examples 49 to 52 except for using a Y type oxotitanylphthalocyanine (CG2-2) as the electric charge generating material, a multi-layer type photosensitive material for digital light source were produced, respectively.

Comparative Examples 22 to 28

According to the same manner as that described in Example 49 except for using stilbene derivatives (6-1) to (6-7) as the hole transferring material, multi-layer type photosensitive materials for digital light source were produced, respectively.

Comparative Examples 29 to 35

According to the same manner as that described in Example 53 except for using stilbene derivatives (6-1) to (6-7) as the hole transferring material, multi-layer type photosensitive materials for digital light source were produced, respectively.

Comparative Examples 36 to 42

According to the same manner as that described in Example 57 except for using stilbene derivatives (6-1) to (6-7) as the hole transferring material, multi-layer type photosensitive materials for digital light source were produced, respectively.

The photosensitive materials obtained in Examples 49 to 60 and Comparative Examples 22 to 42 were subjected to the following electrical characteristics test (II) and the electrical characteristics of the respective photosensitive materials were evaluated, respectively.

Electrical Characteristics Test (II)

According to the same manner as that described in the above electrical characteristics test (I) except for charging the surface of the photosensitive material to −700 V±20 V, the residual potential $V_r$ (V) and half-life exposure $E_{1/2}$ ($\mu$J/cm$^2$) were determined.

The kind of the electric charge generating material, hole transferring material and electron transferring material used in the above respective Examples and Comparative Examples as well as test results of the electrical characteristics are shown in Tables 8 and 9.

TABLE 8

| | Electric charge generating material | Hole transferring material | $V_o$ | $V_r$ | $E_{1/2}$ |
|---|---|---|---|---|---|
| Example 49 | CG1-1 | 11-2 | −700 | −130 | 0.61 |
| Example 50 | CG1-1 | 11-6 | −702 | −129 | 0.61 |
| Example 51 | CG1-1 | 12-6 | −703 | −129 | 0.60 |
| Example 52 | CG1-1 | 13-6 | −701 | −137 | 0.63 |
| Example 53 | CG2-1 | 11-2 | −700 | −107 | 0.57 |
| Example 54 | CG2-1 | 11-6 | −699 | −107 | 0.57 |
| Example 55 | CG2-1 | 12-6 | −700 | −106 | 0.56 |
| Example 56 | CG2-1 | 13-6 | −701 | −111 | 0.59 |
| Example 57 | CG2-2 | 11-2 | −702 | −97 | 0.41 |
| Example 58 | CG2-2 | 11-6 | −703 | −98 | 0.42 |
| Example 59 | CG2-2 | 12-6 | −704 | −97 | 0.41 |
| Example 60 | CG2-2 | 13-6 | −702 | −106 | 0.51 |

TABLE 9

| | Electric charge generating material | Hole transferring material | $V_o$ | $V_r$ | $E_{1/2}$ |
|---|---|---|---|---|---|
| Comp. Example 22 | CG1-1 | 6-1 | −700 | −160 | 0.76 |
| Comp. Example 23 | CG1-1 | 6-2 | −702 | −161 | 0.71 |
| Comp. Example 24 | CG1-1 | 6-3 | −703 | −162 | 0.75 |
| Comp. Example 25 | CG1-1 | 6-4 | −704 | −171 | 0.80 |
| Comp. Example 26 | CG1-1 | 6-5 | −700 | −162 | 0.75 |
| Comp. Example 27 | CG1-1 | 6-6 | −702 | −164 | 0.76 |
| Comp. Example 28 | CG1-1 | 6-7 | −701 | −160 | 0.76 |
| Comp. Example 29 | CG2-1 | 6-1 | −699 | −159 | 0.74 |
| Comp. Example 30 | CG2-1 | 6-2 | −700 | −158 | 0.74 |
| Comp. Example 31 | CG2-1 | 6-3 | −700 | −161 | 0.75 |
| Comp. Example 32 | CG2-1 | 6-4 | −703 | −169 | 0.79 |
| Comp. Example 33 | CG2-1 | 6-5 | −700 | −158 | 0.74 |
| Comp. Example 34 | CG2-1 | 6-6 | −701 | −161 | 0.75 |
| Comp. Example 35 | CG2-1 | 6-7 | −701 | −157 | 0.73 |
| Comp. Example 36 | CG2-2 | 6-1 | −699 | −155 | 0.74 |
| Comp. Example 37 | CG2-2 | 6-2 | −699 | −156 | 0.74 |
| Comp. Example 38 | CG2-2 | 6-3 | −702 | −165 | 0.76 |
| Comp. Example 39 | CG2-2 | 6-4 | −701 | −157 | 0.73 |
| Comp. Example 40 | CG2-2 | 6-5 | −703 | −160 | 0.75 |
| Comp. Example 41 | CG2-2 | 6-6 | −701 | −165 | 0.77 |
| Comp. Example 42 | CG2-2 | 6-7 | −700 | −157 | 0.74 |

Single-Layer Type Photosensitive Material for Analogue Light Source

Examples 61 to 64

According to the same manner as that described in Examples 1 to 4 except for using a perylene pigment represented by the formula (CG3-1):

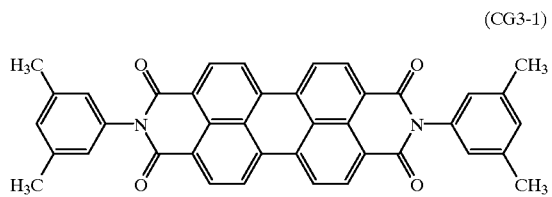

(CG3-1)

as the electric charge generating material, single-layer type photosensitive materials for analogue light source were produced, respectively.

Examples 65 to 68

According to the same manner as that described in Examples 5 to 8 except for using a perylene pigment represented by the formula (CG3-1) as the electric charge generating material, single-layer type photosensitive materials for analogue light source were produced, respectively.

Examples 69 to 72

According to the same manner as that described in Examples 9 to 12 except for using a perylene pigment represented by the formula (CG3-1) as the electric charge generating material, single-layer type photosensitive materials for analogue light source were produced, respectively.

Examples 73 to 76

According to the same manner as that described in Examples 13 to 16 except for using a perylene pigment represented by the formula (CG3-1) as the electric charge generating material, single-layer type photosensitive materials for analogue light source were produced, respectively.

Comparative Examples 43 to 49

According to the same manner as that described in Comparative Examples 1 to 7 except for using a perylene pigment represented by the formula (CG3-1) as the electric charge generating material, single-layer type photosensitive materials for analogue light source were produced, respectively.

The photosensitive materials obtained in Examples 61 to 76 and Comparative Examples 43 to 49 were subjected to the following electrical characteristics test (III) and the electrical characteristics of the respective photosensitive materials were evaluated, respectively.

Electrical Characteristics Test (III)

According to the same manner as that described in the above electrical characteristics test (I) except for using white light (light intensity: 8 lux) from a halogen lamp as an exposure light source, the surface potential $V_o$ (V), residual potential $V_r$ (V) and half-life exposure $E_{1/2}$ (lux.second) were determined.

The kind of the electric charge generating material, hole transferring material and electron transferring material used in the above respective Examples and Comparative Examples as well as test results of the electrical characteristics are shown in Table 10.

TABLE 10

| | Electric charge generating material | Hole transferring material | Electron transferring material | $V_o$ | $V_r$ | $E_{1/2}$ |
|---|---|---|---|---|---|---|
| Example 61 | CG3-1 | 11-2 | — | 700 | 210 | 1.60 |
| Example 62 | CG3-1 | 11-6 | — | 703 | 210 | 1.59 |
| Example 63 | CG3-1 | 12-6 | — | 701 | 211 | 1.60 |
| Example 64 | CG3-1 | 13-6 | — | 702 | 215 | 1.63 |
| Example 65 | CG3-1 | 11-2 | ET17-1 | 699 | 185 | 1.50 |
| Example 66 | CG3-1 | 11-6 | ET17-1 | 701 | 184 | 1.49 |
| Example 67 | CG3-1 | 12-6 | ET17-1 | 702 | 183 | 1.49 |
| Example 68 | CG3-1 | 13-6 | ET17-1 | 699 | 191 | 1.55 |
| Example 69 | CG3-1 | 11-2 | ET14-1 | 698 | 181 | 1.47 |
| Example 70 | CG3-1 | 11-6 | ET14-1 | 700 | 180 | 1.47 |
| Example 71 | CG3-1 | 12-6 | ET14-1 | 702 | 179 | 1.46 |
| Example 72 | CG3-1 | 13-6 | ET14-1 | 701 | 188 | 1.52 |
| Example 73 | CG3-1 | 11-2 | ET14-2 | 698 | 176 | 1.46 |
| Example 74 | CG3-1 | 11-6 | ET14-2 | 702 | 175 | 1.46 |
| Example 75 | CG3-1 | 12-6 | ET14-2 | 701 | 174 | 1.45 |
| Example 76 | CG3-1 | 13-6 | ET14-2 | 703 | 181 | 1.48 |
| Comp. Example 43 | CG3-1 | 6-1 | — | 695 | 241 | 1.77 |
| Comp. Example 44 | CG3-1 | 6-2 | — | 701 | 240 | 1.77 |

TABLE 10-continued

| | Electric charge generating material | Hole trans- ferring material | Electron trans- ferring material | $V_o$ | $V_r$ | $E_{1/2}$ |
|---|---|---|---|---|---|---|
| Comp. Example 45 | CG3-1 | 6-3 | — | 700 | 241 | 1.76 |
| Comp. Example 46 | CG3-1 | 6-4 | — | 702 | 251 | 1.79 |
| Comp. Example 47 | CG3-1 | 6-5 | — | 703 | 241 | 1.77 |
| Comp. Example 48 | CG3-1 | 6-6 | — | 701 | 247 | 1.78 |
| Comp. Example 49 | CG3-1 | 6-7 | — | 700 | 243 | 1.77 |

Examples 77 to 80

According to the same manner as that described in Examples 61 to 64 except for using a bisazo pigment represented by the formula (CG4-1):

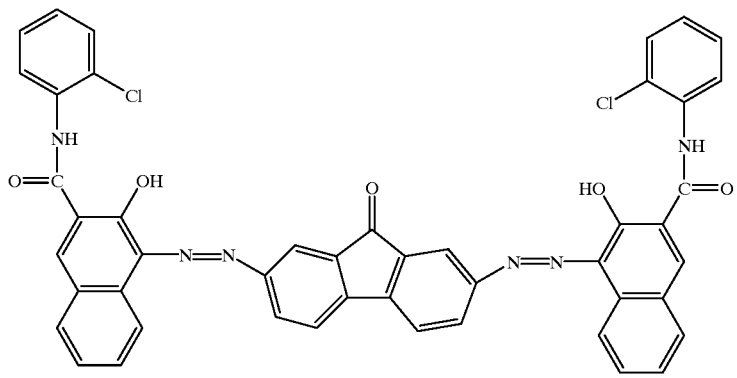

(CG4-1)

as the electric charge generating material, single-layer type photosensitive materials for analogue light source were produced, respectively.

Examples 81 to 84

According to the same manner as that described in Examples 65 to 68 except for using a bisazo pigment represented by the formula (CG4-1) as the electric charge generating material, single-layer type photosensitive materials for analogue light source were produced, respectively.

Examples 85 to 88

According to the same manner as that described in Examples 69 to 72 except for using a bisazo pigment represented by the formula (CG4-1) as the electric charge generating material, single-layer type photosensitive materials for analogue light source were produced, respectively.

Examples 89 to 92

According to the same manner as that described in Examples 73 to 76 except for using a bisazo pigment represented by the formula (CG4-1) as the electric charge generating material, single-layer type photosensitive materials for analogue light source were produced, respectively.

Comparative Examples 50 to 56

According to the same manner as that described in Comparative Examples 43 to 49 except for using a bisazo pigment represented by the formula (CG4-1) as the electric charge generating material, single-layer type photosensitive materials for analogue light source were produced, respectively.

The photosensitive materials obtained in Examples 77 to 92 and Comparative Examples 50 to 56 were subjected to the above electrical characteristics test (III) and the electrical characteristics of the respective photosensitive materials were evaluated, respectively. The kind of the electric charge generating material, hole transferring material and electron transferring material used in the above respective Examples and Comparative Examples as well as test results of the electrical characteristics are shown in Table 11.

TABLE 11

| | Electric charge generating material | Hole trans- ferring material | Electron trans- ferring material | $V_o$ | $V_r$ | $E_{1/2}$ |
|---|---|---|---|---|---|---|
| Example 77 | CG4-1 | 11-2 | — | 701 | 180 | 1.50 |
| Example 78 | CG4-1 | 11-6 | — | 703 | 179 | 1.50 |
| Example 79 | CG4-1 | 12-6 | — | 702 | 181 | 1.49 |
| Example 80 | CG4-1 | 13-6 | — | 700 | 187 | 1.55 |
| Example 81 | CG4-1 | 11-2 | ET17-1 | 699 | 156 | 1.38 |
| Example 82 | CG4-1 | 11-6 | ET17-1 | 699 | 154 | 1.39 |
| Example 83 | CG4-1 | 12-6 | ET17-1 | 700 | 153 | 1.39 |
| Example 84 | CG4-1 | 13-6 | ET17-1 | 703 | 160 | 1.41 |
| Example 85 | CG4-1 | 11-2 | ET14-1 | 701 | 150 | 1.38 |
| Example 86 | CG4-1 | 11-6 | ET14-1 | 702 | 149 | 1.37 |
| Example 87 | CG4-1 | 12-6 | ET14-1 | 705 | 149 | 1.37 |
| Example 88 | CG4-1 | 13-6 | ET14-1 | 700 | 157 | 1.41 |
| Example 89 | CG4-1 | 11-2 | ET14-2 | 702 | 139 | 1.31 |
| Example 90 | CG4-1 | 11-6 | ET14-2 | 705 | 137 | 1.30 |
| Example 91 | CG4-1 | 12-6 | ET14-2 | 699 | 138 | 1.31 |
| Example 92 | CG4-1 | 13-6 | ET14-2 | 700 | 147 | 1.36 |
| Comp. Example 50 | CG4-1 | 6-1 | — | 701 | 200 | 1.59 |
| Comp. Example 51 | CG4-1 | 6-2 | — | 701 | 203 | 1.60 |
| Comp. Example 52 | CG4-1 | 6-3 | — | 700 | 202 | 1.60 |
| Comp. Example 53 | CG4-1 | 6-4 | — | 702 | 215 | 1.72 |
| Comp. Example 54 | CG4-1 | 6-5 | — | 703 | 204 | 1.60 |
| Comp. Example 55 | CG4-1 | 6-6 | — | 701 | 211 | 1.71 |
| Comp. Example 56 | CG4-1 | 6-7 | — | 700 | 201 | 1.60 |

Examples 93 to 96

According to the same manner as that described in Examples 61 to 64 except for using a bisazo pigment represented by the formula (CG4-2):

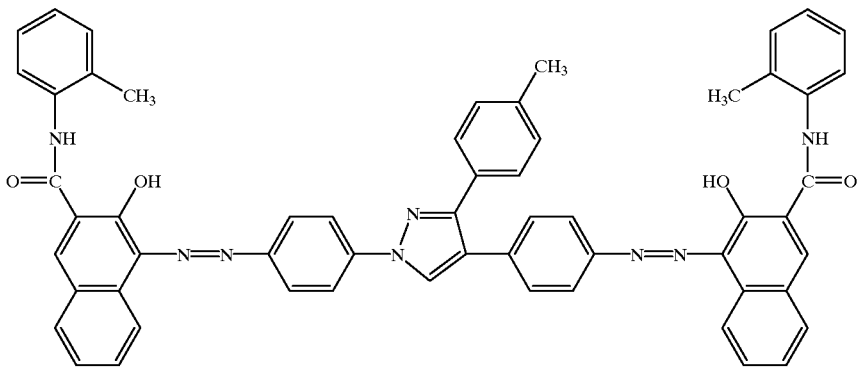

(CG4-2)

as the electric charge generating material, single-layer type photosensitive materials for analogue light source were produced, respectively.

Examples 97 to 100

According to the same manner as that described in Examples 65 to 68 except for using a bisazo pigment represented by the formula (CG4-2) as the electric charge generating material, single-layer type photosensitive materials for analogue light source were produced, respectively.

Examples 101 to 104

According to the same manner as that described in Examples 69 to 72 except for using a bisazo pigment represented by the formula (CG4-2) as the electric charge generating material, single-layer type photosensitive materials for analogue light source were produced, respectively.

Examples 105 to 108

According to the same manner as that described in Examples 73 to 76 except for using a bisazo pigment represented by the formula (CG4-2) as the electric charge generating material, single-layer type photosensitive materials for analogue light source were produced, respectively.

Comparative Examples 57 to 63

According to the same manner as that described in Comparative Examples 43 to 49 except for using a bisazo pigment represented by the formula (CG4-2) as the electric charge generating material, single-layer type photosensitive materials for analogue light source were produced, respectively.

The photosensitive materials obtained in Examples 93 to 108 and Comparative Examples 57 to 63 were subjected to the above electrical characteristics test (III) and the electrical characteristics of the respective photosensitive materials were evaluated, respectively. The kind of the electric charge generating material, hole transferring material and electron transferring material used in the above respective Examples and Comparative Examples as well as test results of the electrical characteristics are shown in Table 12.

TABLE 12

| | Electric charge generating material | Hole trans- ferring material | Electron trans- ferring material | $V_o$ | $V_r$ | $E_{1/2}$ |
|---|---|---|---|---|---|---|
| Example 93 | CG4-2 | 11-2 | — | 700 | 205 | 1.61 |
| Example 94 | CG4-2 | 11-6 | — | 701 | 203 | 1.60 |
| Example 95 | CG4-2 | 12-6 | — | 702 | 204 | 1.60 |
| Example 96 | CG4-2 | 13-6 | — | 702 | 211 | 1.65 |
| Example 97 | CG4-2 | 11-2 | ET17-1 | 700 | 180 | 1.54 |
| Example 98 | CG4-2 | 11-6 | ET17-1 | 703 | 177 | 1.52 |
| Example 99 | CG4-2 | 12-6 | ET17-1 | 699 | 178 | 1.52 |
| Example 100 | CG4-2 | 13-6 | ET17-1 | 698 | 186 | 1.57 |
| Example 101 | CG4-2 | 11-2 | ET14-1 | 702 | 167 | 1.44 |
| Example 102 | CG4-2 | 11-6 | ET14-1 | 701 | 166 | 1.43 |
| Example 103 | CG4-2 | 12-6 | ET14-1 | 703 | 166 | 1.44 |
| Example 104 | CG4-2 | 13-6 | ET14-1 | 700 | 171 | 1.49 |
| Example 105 | CG4-2 | 11-2 | ET14-2 | 701 | 160 | 1.39 |
| Example 106 | CG4-2 | 11-6 | ET14-2 | 700 | 160 | 1.39 |
| Example 107 | CG4-2 | 12-6 | ET14-2 | 702 | 158 | 1.37 |
| Example 108 | CG4-2 | 13-6 | ET14-2 | 700 | 167 | 1.44 |
| Comp. Example 57 | CG4-2 | 6-1 | — | 704 | 227 | 1.75 |
| Comp. Example 58 | CG4-2 | 6-2 | — | 703 | 230 | 1.76 |
| Comp. Example 59 | CG4-2 | 6-3 | — | 702 | 232 | 1.78 |
| Comp. Example 60 | CG4-2 | 6-4 | — | 701 | 241 | 1.81 |
| Comp. Example 61 | CG4-2 | 6-5 | — | 701 | 233 | 1.79 |
| Comp. Example 62 | CG4-2 | 6-6 | — | 702 | 240 | 1.80 |
| Comp. Example 63 | CG4-2 | 6-7 | — | 700 | 229 | 1.76 |

Examples 109 to 112

According to the same manner as that described in Examples 61 to 64 except for using a bisazo pigment represented by the formula (CG4-3):

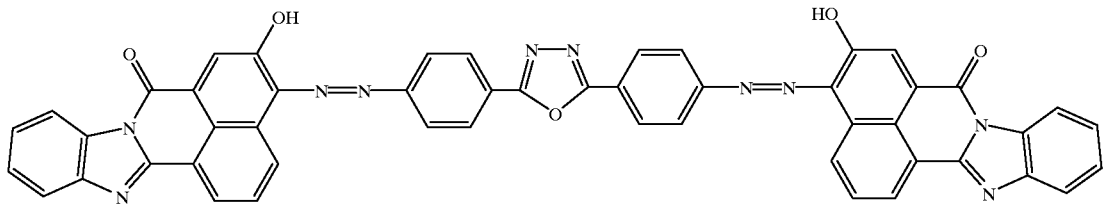
(CG4-3)

as the electric charge generating material, single-layer type photosensitive materials for analogue light source were produced, respectively.

Examples 113 to 116

According to the same manner as that described in Examples 65 to 68 except for using a bisazo pigment represented by the formula (CG4-3) as the electric charge generating material, single-layer type photosensitive materials for analogue light source were produced, respectively.

Examples 117 to 120

According to the same manner as that described in Examples 69 to 72 except for using a bisazo pigment represented by the formula (CG4-3) as the electric charge generating material, single-layer type photosensitive materials for analogue light source were produced, respectively.

Examples 121 to 124

According to the same manner as that described in Examples 73 to 76 except for using a bisazo pigment represented by the formula (CG4-3) as the electric charge generating material, single-layer type photosensitive materials for analogue light source were produced, respectively.

Comparative Examples 64 to 70

According to the same manner as that described in Comparative Examples 43 to 49 except for using a bisazo pigment represented by the formula (CG4-3) as the electric charge generating material, single-layer type photosensitive materials for analogue light source were produced, respectively.

The photosensitive materials obtained in Examples 109 to 124 and Comparative Examples 64 to 70 were subjected to the above electrical characteristics test (III) and the electrical characteristics of the respective photosensitive materials were evaluated, respectively. The kind of the electric charge generating material, hole transferring material and electron transferring material used in the above respective Examples and Comparative Examples as well as test results of the electrical characteristics are shown in Table 13.

TABLE 13

| | Electric charge generating material | Hole trans- ferring material | Electron trans- ferring material | $V_o$ | $V_r$ | $E_{1/2}$ |
|---|---|---|---|---|---|---|
| Example 109 | CG4-3 | 11-2 | — | 701 | 205 | 1.67 |
| Example 110 | CG4-3 | 11-6 | — | 703 | 204 | 1.67 |
| Example 111 | CG4-3 | 12-6 | — | 702 | 204 | 1.67 |
| Example 112 | CG4-3 | 13-6 | — | 701 | 210 | 1.70 |

TABLE 13-continued

| | Electric charge generating material | Hole trans- ferring material | Electron trans- ferring material | $V_o$ | $V_r$ | $E_{1/2}$ |
|---|---|---|---|---|---|---|
| Example 113 | CG4-3 | 11-2 | ET17-1 | 704 | 180 | 1.53 |
| Example 114 | CG4-3 | 11-6 | ET17-1 | 699 | 179 | 1.52 |
| Example 115 | CG4-3 | 12-6 | ET17-1 | 700 | 180 | 1.52 |
| Example 116 | CG4-3 | 13-6 | ET17-1 | 703 | 191 | 1.54 |
| Example 117 | CG4-3 | 11-2 | ET14-1 | 705 | 185 | 1.50 |
| Example 118 | CG4-3 | 11-6 | ET14-1 | 697 | 182 | 1.49 |
| Example 119 | CG4-3 | 12-6 | ET14-1 | 704 | 183 | 1.49 |
| Example 120 | CG4-3 | 13-6 | ET14-1 | 700 | 191 | 1.63 |
| Example 121 | CG4-3 | 11-2 | ET14-2 | 703 | 182 | 1.54 |
| Example 122 | CG4-3 | 11-6 | ET14-2 | 702 | 179 | 1.52 |
| Example 123 | CG4-3 | 12-6 | ET14-2 | 700 | 181 | 1.52 |
| Example 124 | CG4-3 | 13-6 | ET14-2 | 701 | 189 | 1.54 |
| Comp. Example 64 | CG4-3 | 6-1 | — | 709 | 231 | 1.75 |
| Comp. Example 65 | CG4-3 | 6-2 | — | 711 | 229 | 1.74 |
| Comp. Example 66 | CG4-3 | 6-3 | — | 710 | 230 | 1.75 |
| Comp. Example 67 | CG4-3 | 6-4 | — | 708 | 244 | 1.80 |
| Comp. Example 68 | CG4-3 | 6-5 | — | 700 | 231 | 1.75 |
| Comp. Example 69 | CG4-3 | 6-6 | — | 700 | 250 | 1.81 |
| Comp. Example 70 | CG4-3 | 6-7 | — | 703 | 231 | 1.75 |

Multi-Layer Type Photosensitive Material for Analogue Light Source

Examples 125 to 128

According to the same manner as that described in Examples 49 to 52 except for using a perylene pigment (CG3-1) as the electric charge generating material, multi-layer type photosensitive materials for analogue light source were produced, respectively.

Examples 129 to 132

According to the same manner as that described in Examples 49 to 52 except for using a bisazo pigment (CG4-1) as the electric charge generating material, multi-layer type photosensitive materials for analogue light source were produced, respectively.

Examples 133 to 136

According to the same manner as that described in Examples 49 to 52 except for using a bisazo pigment (CG4-2) as the electric charge generating material, multi-layer type photosensitive materials for analogue light source were produced, respectively.

Examples 137 to 140

According to the same manner as that described in Examples 49 to 52 except for using a bisazo pigment (CG4-3) as the electric charge generating material, multi-layer type photosensitive materials for analogue light source were produced, respectively.

Comparative Examples 71 to 76

According to the same manner as that described in Example 125 except for using stilbene derivatives (6-1) to (6-6) as the hole transferring material, multi-layer type photosensitive materials for analogue light source were produced, respectively.

Comparative Examples 77 to 82

According to the same manner as that described in Example 129 except for using stilbene derivatives (6-1) to (6-6) as the hole transferring material, multi-layer type photosensitive materials for analogue light source were produced, respectively.

Comparative Examples 83 to 88

According to the same manner as that described in Example 133 except for using stilbene derivatives (6-1) to (6-6) as the hole transferring material, multi-layer type photosensitive materials for analogue light source were produced, respectively.

Comparative Examples 89 to 95

According to the same manner as that described in Example 137 except for using stilbene derivatives (6-1) to (6-7) as the hole transferring-material, multi-layer type photosensitive materials for analogue light source were produced, respectively.

The photosensitive materials obtained in Examples 125 to 140 and Comparative Examples 71 to 95 were subjected to the following electrical characteristics test (IV) and the electrical characteristics of the respective photosensitive materials were evaluated, respectively.

Electrical Characteristics Test (IV)

According to the same manner as that described in the above electrical characteristics test (III) except for charging the surface of the photosensitive material to $-700$ V$\pm 20$ V, the surface potential $V_o$ (V), residual potential $V_r$ (V) and half-life exposure $E_{1/2}$ (lux.sec) were determined.

The kind of the electric charge generating material, hole transferring material and electron transferring material used in the above respective Examples and Comparative Examples as well as test results of the electrical characteristics are shown in Tables 14 and 15.

TABLE 14

| | Electric charge generating material | Hole transferring material | $V_o$ | $V_r$ | $E_{1/2}$ |
|---|---|---|---|---|---|
| Example 125 | CG3-1 | 11-2 | −701 | −130 | 1.92 |
| Example 126 | CG3-1 | 11-6 | −702 | −128 | 1.89 |
| Example 127 | CG3-1 | 12-6 | −700 | −127 | 1.88 |
| Example 128 | CG3-1 | 13-6 | −700 | −140 | 1.97 |
| Example 129 | CG4-1 | 11-2 | −698 | −110 | 1.84 |
| Example 130 | CG4-1 | 11-6 | −700 | −109 | 1.83 |
| Example 131 | CG4-1 | 12-6 | −703 | −107 | 1.82 |
| Example 132 | CG4-1 | 13-6 | −701 | −117 | 1.86 |
| Example 133 | CG4-2 | 11-2 | −702 | −123 | 1.87 |
| Example 134 | CG4-2 | 11-6 | −700 | −121 | 1.87 |
| Example 135 | CG4-2 | 12-6 | −701 | −121 | 1.87 |
| Example 136 | CG4-2 | 13-6 | −700 | −129 | 1.89 |
| Example 137 | CG4-3 | 11-2 | −699 | −105 | 1.81 |
| Example 138 | CG4-3 | 11-6 | −701 | −104 | 1.81 |
| Example 139 | CG4-3 | 12-6 | −702 | −105 | 1.80 |
| Example 140 | CG4-3 | 13-6 | −703 | −110 | 1.84 |

TABLE 15

| | Electric charge generating material | Hole transferring material | $V_o$ | $V_r$ | $E_{1/2}$ |
|---|---|---|---|---|---|
| Comp. Example 71 | CG3-1 | 6-1 | −701 | −157 | 2.01 |
| Comp. Example 72 | CG3-1 | 6-2 | −704 | −161 | 2.11 |
| Comp. Example 73 | CG3-1 | 6-3 | −704 | −167 | 2.13 |
| Comp. Example 74 | CG3-1 | 6-4 | −703 | −169 | 2.15 |
| Comp. Example 75 | CG3-1 | 6-5 | −700 | −161 | 2.12 |
| Comp. Example 76 | CG3-1 | 6-6 | −701 | −171 | 2.16 |
| Comp. Example 77 | CG4-1 | 6-1 | −702 | −157 | 2.02 |
| Comp. Example 78 | CG4-1 | 6-2 | −700 | −154 | 2.13 |
| Comp. Example 79 | CG4-1 | 6-3 | −703 | −167 | 2.13 |
| Comp. Example 80 | CG4-1 | 6-4 | −701 | −169 | 2.15 |
| Comp. Example 81 | CG4-1 | 6-5 | −699 | −157 | 2.01 |
| Comp. Example 82 | CG4-1 | 6-6 | −701 | −155 | 2.01 |
| Comp. Example 83 | CG4-2 | 6-1 | −702 | −155 | 2.01 |
| Comp. Example 84 | CG4-2 | 6-2 | −698 | −154 | 2.02 |
| Comp. Example 85 | CG4-2 | 6-3 | −702 | −162 | 2.10 |
| Comp. Example 86 | CG4-2 | 6-4 | −701 | −167 | 2.13 |
| Comp. Example 87 | CG4-2 | 6-5 | −701 | −158 | 2.01 |
| Comp. Example 88 | CG4-2 | 6-6 | −700 | −155 | 2.01 |
| Comp. Example 89 | CG4-3 | 6-1 | −703 | −158 | 2.02 |
| Comp. Example 90 | CG4-3 | 6-2 | −702 | −157 | 2.01 |
| Comp. Example 91 | CG4-3 | 6-3 | −701 | −168 | 2.13 |
| Comp. Example 92 | CG4-3 | 6-4 | −704 | −171 | 2.16 |
| Comp. Example 93 | CG4-3 | 6-5 | −703 | −154 | 2.02 |
| Comp. Example 94 | CG4-3 | 6-6 | −701 | −157 | 2.03 |
| Comp. Example 95 | CG4-3 | 6-7 | −700 | −159 | 2.02 |

As is apparent from Tables 5 to 15, regarding the electrophotosensitive materials of Examples 1 to 140, an absolute value of the residual potential $V_r$ is smaller than that of the Comparative Examples corresponding to the respective Examples. The half-life exposure $E_{1/2}$ is the same as or smaller than that of the Comparative Examples corresponding to the respective Examples. Consequently, it is apparent that the electrophotosensitive materials of Examples 1 to 140 have excellent sensitivity.

When electrophotosensitive materials (single-layer and multi-layer type photosensitive materials for analogue light source, and single-layer and multi-layer type photosensitive materials for digital light source) are produced by using the stilbene derivative in Synthesis Examples 6 to 27 according to the same manner as that described in Examples 1 to 140, a photosensitive material having excellent sensitivity, which is the same as that of the electrophotosensitive materials of Examples 1 to 140.

The disclosure of Japanese Patent Application Serial No.10-308878, filed on Oct. 29, 1998, is incorporated herein by reference.

What is claimed is:

1. A stilbene derivative represented by the general formula (1):

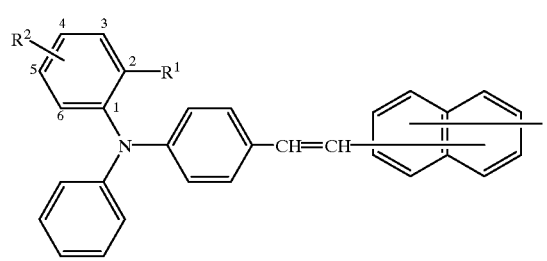

(1)

-continued

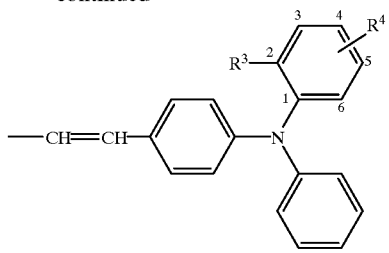

wherein $R^1$ and $R^3$ are the same or different and represent an alkyl group which may have a substituent, an aryl group which may have a substituent, an aralkyl group which may have a substituent, or an alkoxy group which may have a substituent, and $R^2$ and $R^4$ are the same or different and represent a hydrogen atom, an alkyl group which may have a substituent, or an alkoxy group which may have a substituent.

2. The stilbene derivative according to claim 1, wherein $R^2$ and $R^4$ are hydrogen atoms when the substitution position of $R^2$ and $R^4$ in the general formula (1) is a 4 (para)-position.

3. The stilbene derivative according to claim 1, wherein $R^3$ and $R^1$ in the general formula (1) are the same groups and $R^4$ and $R^2$ are the same groups.

4. The stilbene derivative according to claim 1, wherein one phenyl group of the diphenylamino group at the molecular end has no substituent while the other phenyl group has a substituent at the 2-/3-positions, 2-/5-positions or 2-/6-positions or has a subsituent only at the 2-position in the general formula (1).

5. The stilbene derivative according to claim 1, wherein the alkyl group corresponding to $R^1$, $R^2$, $R^3$ and $R^4$ is an alkyl group having 1 to 6 carbon atoms.

6. The stilbene derivative according to claim 1, wherein the aryl group corresponding to $R^1$ and $R^3$ is phenyl, naphthyl, anthryl or phenanthryl.

7. The stilbene derivative according to claim 1, wherein the aralkyl group corresponding to $R^1$ and $R^3$ is an aralkyl group whose alkyl portion has 1 to 6 carbon atoms.

8. The stilbene derivative according to claim 1, wherein the alkoxy group corresponding to $R^1$, $R^2$, $R^3$ and $R^4$ is an alkoxy group having 1 to 6 carbon atoms.

9. The stilbene derivative according to claim 1, wherein the stilbene derivatives are stilbene derivative represented by the general formulas (11) to (13):

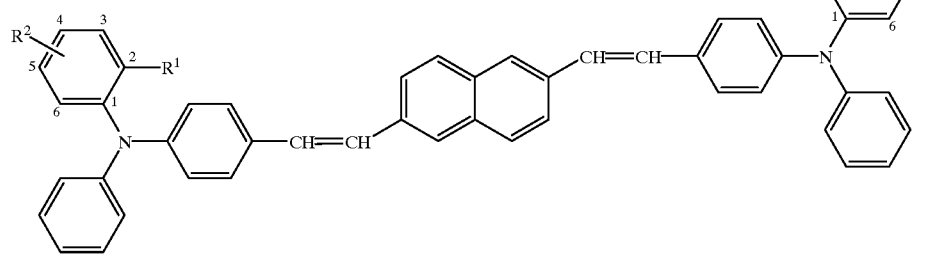
(11)

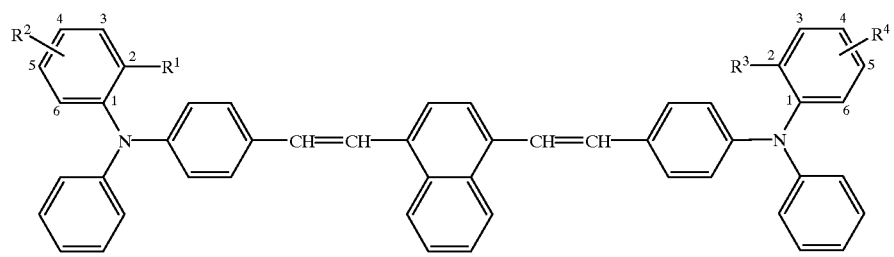
(12)

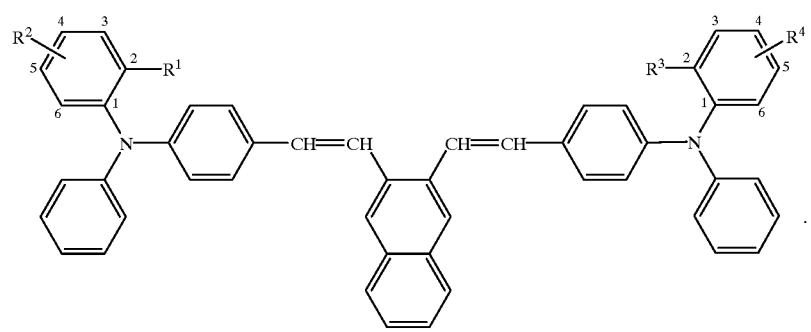
(13)

10. A method of producing the stilbene derivative of claim 3, which comprises reacting a formylated triphenylamine derivative represented by the general formula (2):

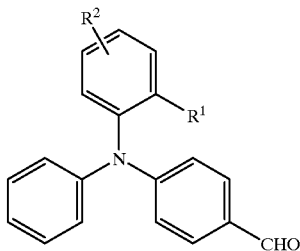
(2)

wherein R¹ represent an alkyl group which may have a substituent, an aryl group which may have a substituent, an aralkyl group which may have a substituent, or an alkoxy group which may have a substituent, and R² represents a hydrogen atom, an alkyl group which may have a substituent, or an alkoxy group which may have a substituent, with a bisphosphate derivative represented by the general formula (3):

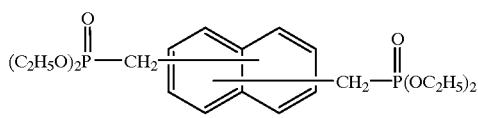
(3)

11. The method according to claim 10, wherein the formylated triphenylamine derivative (2) is obtained by reacting an aniline derivative represented by the general formula (4):

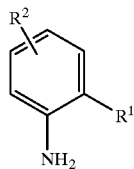
(4)

wherein R¹ represent an alkyl group which may have a substituent, an aryl group which may have a substituent, an aralkyl group which may have a substituent, or an alkoxy group which may have a substituent, and R² represents a hydrogen atom, an alkyl group which may have a substituent, or an alkoxy group which may have a substituent, with iodobenzene to obtain a triphenylamine derivative represented by the general formula (5):

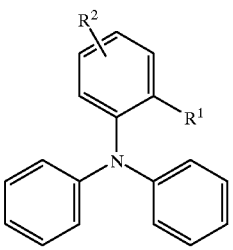
(5)

wherein R¹ represent an alkyl group which may have a substituent, an aryl group which may have a substituent, an aralkyl group which may have a substituent, or an alkoxy group which may have a substituent, and R² represents a hydrogen atom, an alkyl group which may have a substituent, or an alkoxy group which may have a substituent, and formylating this compound (5) by using the Vilsmeier method.

12. An electrophotosensitive material comprising a conductive substrate and a photosensitive layer provided on the conductive substrate, wherein the photosensitive layer contains the stilbene derivative represented by the general formula (1) of any one of claims 1 to 9.

13. The electrophotosensitive material according to claim 12, wherein the photosensitive layer is a single-layer type photosensitive layer containing an electric charge generating material and an electron transferring material, together with the stilbene derivative represented by the general formula (1) of any one of claims 1 to 9.

\* \* \* \* \*